US012599619B2

(12) United States Patent
Wei

(10) Patent No.: US 12,599,619 B2
(45) Date of Patent: Apr. 14, 2026

(54) METHOD OF TREATING BLEPHARITIS OR CONJUNCTIVITIS

(71) Applicant: IVIEW THERAPEUTICS, INC., Cranbury, NJ (US)

(72) Inventor: Edward T. Wei, Berkeley, CA (US)

(73) Assignee: IVIEW THERAPEUTICS, INC., Cranbury, NJ (US)

( * ) Notice: Subject to any disclaimer, the term of this patent is extended or adjusted under 35 U.S.C. 154(b) by 1002 days.

(21) Appl. No.: 17/803,311

(22) Filed: May 3, 2022

(65) Prior Publication Data

US 2022/0265687 A1 Aug. 25, 2022

Related U.S. Application Data

(63) Continuation-in-part of application No. 16/350,559, filed on Nov. 30, 2018, now Pat. No. 12,029,743.

(51) Int. Cl.

| | |
|---|---|
| ***A61K 31/662*** | (2006.01) |
| ***A61K 9/00*** | (2006.01) |
| ***A61K 31/66*** | (2006.01) |
| ***A61P 17/04*** | (2006.01) |
| ***A61P 27/02*** | (2006.01) |
| ***A61P 27/04*** | (2006.01) |

(52) U.S. Cl.

CPC .......... *A61K 31/662* (2013.01); *A61K 9/0014* (2013.01); *A61K 9/0048* (2013.01); *A61P 17/04* (2018.01)

(58) Field of Classification Search

None

See application file for complete search history.

(56) References Cited

U.S. PATENT DOCUMENTS

| | | | | |
|---|---|---|---|---|
| 2005/0059639 A1* | 3/2005 | Wei | A61K 31/66 514/142 |
| 2013/0177522 A1* | 7/2013 | Liang | A61P 27/04 424/78.04 |
| 2015/0290029 A1* | 10/2015 | Wei | A61F 9/0008 514/75 |
| 2017/0136045 A1* | 5/2017 | Wei | C07F 9/5304 |
| 2017/0266294 A1* | 9/2017 | Baldwin | A61K 9/0048 |

OTHER PUBLICATIONS

Yoon HJ, Kim J, Yang JM, Wei ET, Kim SJ, Yoon KC. Topical TRPM8 Agonist for Relieving Neuropathic Ocular Pain in Patients with Dry Eye: A Pilot Study. J Clin Med. 2021;10:250.

Chung BY, Um JY, Kim JC, Kang SY, Park CW, Kim HO. Pathophysiology and treatment of pruritus in elderly. Int J Mol Sci. 2021;22:1-12.

Chung BY, Kim HB, Jung MJ, Kang SY, Kwak I-S, Park CW, et al. Molecular Sciences Post-Burn Pruritus. 2020;1-15.

* cited by examiner

*Primary Examiner* — Bethany P Barham

*Assistant Examiner* — Peter Anthopolos

(74) *Attorney, Agent, or Firm* — Weisun Rao; Jun Chen; Venture Partner, LLC

(57) ABSTRACT

The present discovery pertains generally to the field of therapeutic compounds. More specifically the present discovery pertains to certain di-isopropyl-phosphinoyl-alkanes as described herein, DIPA-1-7, DIPA-1-8, and DIPA-1-9, collectively referred to herein as "DIPA compounds", that are useful, for example, in the treatment of the discomforts of dermatological disorders (e.g., diseases) The treatment is for the dysesthesia (e.g., caused by irritation, itch, or pain) due to dermatitis, urticaria; scalp itch; vulvar itch; lichen sclerosus; cholestatic itch; psoriasis; sebhorrheic dermatitis; allergic conjunctivitis; blepharitis; and pruritus of the elderly. The applicant has found that topical delivery of DIPA compounds to the skin alleviates the dysesthesia of these conditions in human subjects. The present discovery pertains to pharmaceutical compositions comprising such compounds, and the use of such compounds and compositions, for example, in the treatment of the dysesthesia of these dermatological disorders.

8 Claims, 7 Drawing Sheets

METHOD OF TREATING BLEPHARITIS OR CONJUNCTIVITIS

CROSS-REFERENCE TO RELATED APPLICATIONS

This application is a continuation-in-part of U.S. application Ser. No. 16/350,559, filed on Nov. 30, 2018, which has received a Notice of Allowance on Feb. 23, 2022.

Applicant: Edward T. Wei, Berkeley, CA (US)

Inventor: Edward T. Wei, Berkeley, CA (US)

BACKGROUND OF THE INVENTION

Field of the Invention

The present discovery pertains generally to the field of therapeutic compounds. More specifically the present discovery pertains to certain di-isopropyl-phosphinoyl-alkanes as described herein (DIPA-1-5, DIPA-1-6, DIPA-1-7, DIPA-1-8, and DIPA-1-9, collectively referred to herein as "DIPA compounds") that are useful, for example, in the treatment of symptoms and disorders (e.g., diseases) of the skin. Examples of symptoms are abnormal sensations such as irritation, burning sensations, itch, or pain, collectively called a skin dysesthesia. Examples of disorders in which the skin is inflamed are atopic dermatitis, contact dermatitis, anogenital dermatitis, lichen sclerosus, blepharitis, conjunctivitis, psoriasis, and seborrheic dermatitis. The skin is also a source of pruritus (itch) when its function is disturbed. Pruritus of the skin occurs in such conditions as urticaria, cholestasis, renal dialysis patients, psychogenic disorders, psoriasis, dermatitis, and eczema. The present invention also pertains to pharmaceutical compositions comprising such compounds, and the use of such compounds and compositions, for example, in therapy.

Description of Related Art

The skin, the largest organ of the body, is composed of three layers, the epidermis, dermis, and subcutaneous layer. The outermost layer, the epidermis, is only about 1 mm thick and is densely infiltrated with nerve endings. The epidermis generates epithelial cells that form the stratum corneum, a layer of dead cells that is impermeable to water. The time for the epidermis to replace itself is about 1.5 months. When the skin is injured the cardinal signs of inflammation are a feeling of heat, redness, swelling, and pain. Injured tissues give rise to sensations of irritation, burning, itch, and pain, collectively called dysesthesia. Itch or pruritus is the sensation that provokes the urge to scratch and is a vexing symptom of skin dysfunction. Itch is a complaint of ~80% of patients who visit a dermatology clinic.

Cooling the body's surfaces refresh the senses, relieve discomfort, attenuate pain, reduce itching, and suppress inflammation. Cooling intensity can be ranked as refreshing cool, chilly, cold, icy cold, to painful cold. Chemicals that cool do not generally change tissue temperatures. Menthol is an example of a chemical cooling agent, but it has limited use as an analgesic or an antipruritic because it is irritating and has a short duration of action. Developments of new cooling agents for itch are hampered by the stratum corneum which is a formidable barrier for drugs penetration to the nerve endings in the epidermis.

The cloning of TRP channels ~25 years ago (1998 to 2002) has increased our understanding of the neuronal circuitry of skin thermosensation and dysesthesia. This work culminated in the Nobel award in 2021 to David Julius and Ardem Patapoutian, the pioneers in this research. Now the language to describe skin pathology is more precise and new drugs are devised to target specific TRP receptors on nerve endings to treat dysesthesia and itching.

Known Phosphine Oxides

The 1-dialkyl-phosphinoyl-alkanes [DAPA] are solvent-like molecules that require several [1 to 3] steps for synthesis. They are also known as trialkylphosphine oxides or dialkylphosphorylalkanes. When two of the alkyl groups in DAPA are isopropyl, the DAPA abbreviation is changed to DIPA [di-isopropyl-phosphinoyl-alkane], Rowsell and Spring [Phosphine oxides having a physiological cooling effect. U.S. Pat. No. 4,070,496. Jan. 24, 1978], described a range of phosphine oxides which have a physiological cooling effect on skin and oral cavity. See, e.g., the table in columns 3 and 4 therein. Ten of the compounds shown therein (Table 1) have one isopropyl group (shown as iso-$C_3H_7$). None of the compounds has two isopropyl groups. Siddall et al. [Simplified preparation of some trisubstituted phosphine oxides. J. Chemical Engineering Data 10: 303-305, 1965] reported the synthesis of 1-di-isopropyl-octane [DIPA-1-8], but Siddall et al. did not examine the bioactivity of this molecule.

TABLE 1

Compounds in Rowsell et al., 1978 P(=O)$R_1R_2R_3$

| # | $R_1$ | $R_2$ | $R_3$ |
|---|---|---|---|
| 2 | n-$C_7H_{15}$ | iso-$C_3H_7$ | sec-$C_4H_9$ |
| 3 | n-$C_8H_{17}$ | iso-$C_3H_7$ | sec-$C_4H_9$ |
| 7 | n-$C_6H_{13}$ | iso-$C_3H_7$ | sec-$C_4H_9$ |
| 8 | n-$C_6H_{13}$ | iso-$C_3H_7$ | cyclo-$C_5H_9$ |
| 11 | n-$C_7H_{15}$ | iso-$C_3H_7$ | cyclo-$C_5H_9$ |
| 12 | n-$C_6H_{13}$ | iso-$C_3H_7$ | iso-$C_5H_{11}$ |
| 15 | n-$C_7H_{15}$ | iso-$C_3H_7$ | iso-$C_5H_{11}$ |
| 26 | n-$C_6H_{13}$ | iso-$C_3H_7$ | n-$C_6H_{13}$ |
| 30 | n-$C_8H_{17}$ | iso-$C_3H_7$ | cyclo $C_5H_9$ |
| 47 | iso-$C_3H_7$ | n-$C_4H_9$ | (n-$C_4H_9$)($C_2H_5$)$CHCH_2$ |

BRIEF SUMMARY OF THE INVENTION

Figure 1:
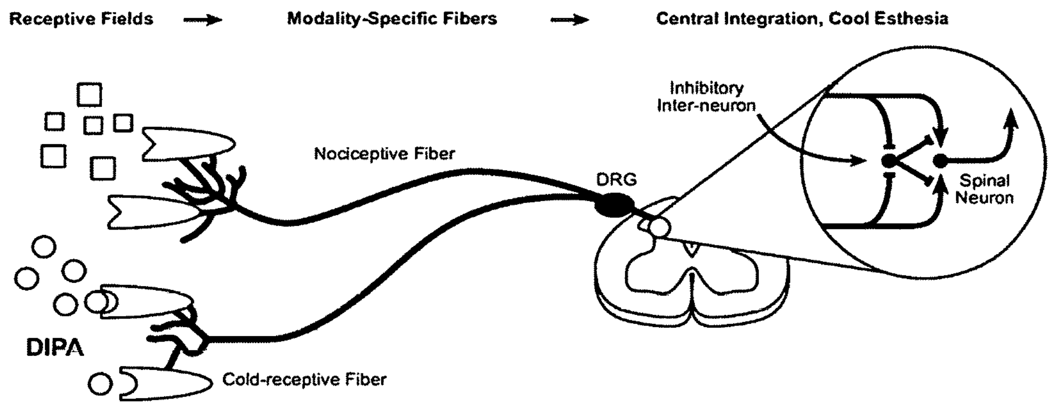
FIG. 1. is an illustration of how DIPA compounds reduce dysesthesia in dermatological disorders, a mechanism called "cool esthesia." Noxious stimuli activate small-diameter C fibers in the peripheral receptive fields, transmitting signals that generate dysesthesia. Application of a DIPA TRPM8 agonist to the receptive field activates larger myelinated Aδ-fibers that transmit signals of coolness (≤25° C.). These signals are modality-specific. The cell bodies of primary afferents are in the peripheral ganglia (DRG=dorsal root ganglion). The afferent signals of nociception and coolness integrate in spinal cord and brainstem nuclei. Cool esthesia occurs when DIPA-induced TRPM8 signals reduce the dysesthesia of nociception.

In this discovery it was noted that structural modification of certain 1-dialkyl-phosphinoyl-alkanes (DAPA) to the 1-di-isopropyl-phosphinoyl-alkane (DIPA) analogs resulted in agents that potently evoke a "dynamic cool" sensation when applied to the skin. The 1-di-isopropyl-phosphinoyl-alkanes described herein are referred to as "DIPA compounds" or "DIPA." The DIPA do not affect tissue temperatures but relieve the dysesthesia and itch of skin injury. The unusual features of DIPA are water-solubility and ease of formulation, penetration through intact skin to reach targets in the epidermis, rapid onset of antipruritic action, and continued efficacy for the treatment of itch after several weeks of use without loss of activity. This relief of dysesthesia and itch is called "cool esthesia" and the proposed neuronal circuity for this mechanism of DIPA action is shown in FIG. 1. New data from clinical trials are presented showing that cool esthesia relieves the itch of urticaria and scalp itch. Additional data show the efficacy of DIPA for the itch of cholestatsis, lichen sclerosus, blepharitis, and conjunctivitis.

FIG. 1. is an illustration of how DIPA compounds reduce dysesthesia in dermatological disorders, a mechanism called "cool esthesia." Noxious stimuli activate small-diameter C fibers in the peripheral receptive fields, transmitting signals that generate dysesthesia. Application of a DIPA TRPM8 agonist to the receptive field activates larger myelinated AS-fibers that transmit signals of coolness (≤25° C.). These signals are modality-specific. The cell bodies of primary afferents are in the peripheral ganglia (DRG=dorsal root ganglia or cranial ganglia). The afferent signals of nociception and coolness integrate in spinal cord and brainstem nuclei. Cool esthesia occurs when DIPA-induced TRPM8 signals reduce the dysesthesia of nociception.

The skin is a frequent site of injury. The cardinal signs of the skin's response to injury (inflammation) are a feeling of heat, redness, swelling, and pain. Over time, the injured tissues give rise to irritation, burning sensations, itch, and pain, collectively called dysesthesia. The DIPA molecules relieve signs of dysesthesia via dynamic cooling. This relief is called "cool esthesia."

Cloning of TRP channels of sensory transmission revolutionized understanding of the neuronal circuitry of thermosensation and dysesthesia. This work culminated in the Nobel award in 2021 to David Julius and Ardem Patapoutian, the pioneers in this research. Now specific TRP receptors may be visualized on nerve endings and mechanisms of drug action rationalized. The emerging view is that dedicated TRPM8 nerve fibers convey the signals of coolness. The sense of cooling (25° C. at the receptor) is anatomically and modality-specific, with its own favored circuitry and cables. The TRPM8-mediated cooling induces "cool esthesia" and counteracts dysesthesia. The neuronal pathways for cooling and dysesthesia need not overlap, but preferably originate from the same dermatome. Signals converge in the spinal cord or brainstem nuclei. Thus, for example, cooling signals from TRPM8 receptive fields in the vulva can suppress vulvar itch. Transmission is via the pudendal nerve from the dermatome of the sacral plexus and into the spinal cord. FIG. 1. illustrates this mechanism and neuronal circuitry.

In layman's terms, the concept of DIPA treatment is like putting a mini-air conditioner onto injured tissues. The unusual property of the DIPA molecules is water solubility and the ability to penetrate the cell layers of the skin to reach receptive targets underneath. The target for delivery is TRPM8. When activated, TRPM8 conveys the cooling sensations. Central integration of these signals relieves dysesthesia. By relieving dysesthesia, the DIPA also has a disease-modifying effect. The patient feels better, sleeps better, and interruption of the itch-scratch allows the tissues to heal. Clinical data in support of these observations are presented. The water solubility of the DIPA at therapeutically effective concentrations facilitates the formulation of compounds for delivery to TRPM8.

Another aspect of the present discovery pertains to a pharmaceutical composition comprising one or more DIPA compounds, as described herein, and a pharmaceutically acceptable carrier or diluent. Particularly preferred embodiments include one or more DIPA compounds and a delivery agent carrying one or more compounds, where the delivery agent is suitable for topical delivery. These preparations, as described herein, may be used in a method of treatment of the human or animal body by therapy, for example, for using a method of treatment of a disorder (e.g., a disease). For example, a preferred embodiment for the relief of vulvar itch is a topical 1% DIPA-1-8 solution in water or saline or a 0.5% gel.

Thus, the discovery proposed a therapeutic method for the treatment of the dysesthesia of a dermatological disorder in a subject in need of treatment thereof, comprising:

topically applying a liquid or semi-liquid composition to the subject's skin, the composition comprising a therapeutically effective amount of one or more compound having Formula 1

Formula 1

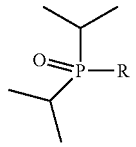

wherein R is n-heptyl, n-octyl or n-nonyl; and wherein the composition, following topical application, penetrates the subject's skin.

DETAILED DESCRIPTION OF THE INVENTION

The present discovery relates to certain compounds (the DIPA compounds described herein) which, when delivered onto the skin, selectively and potently evoke sensations of "dynamic cool" or cool esthesia for at least several hours. The dynamic cool can be repeated without significant diminution of the effects and can be sustained for the whole day. Thus, these compounds have applications in the treatment of skin discomfort, especially skin irritation, itch, and pain.

The structures of the preferred embodiments are shown below. The water-soluble compounds [e.g., 1-di-isopropyl-phosphinoyl-heptane, abbreviated as DIPA-1-7] potently [<5 mg per dose] and rapidly produce on skin robust and intense cooling sensations. This type of drug action is unusual and has not been previously recognized to be achievable on skin surfaces with a stratum corneum (keratinized skin) and has led to new applications as described herein. A chemical feature, the minimum active alkyl side chain adjacent to the phosphine oxide, allows greater exposure of the polar phosphine oxide group to water, and increases water solubility.

Terminology (Arranged Alphabetically)

Allergic Conjunctivitis. Approximately 15% of the world population has allergic disease with ocular involvement. (Leonardi A. Allergy and allergic mediators in tears. Exp Eye Res. 2013; 117:106-17). Allergic conjunctivitis is a localized allergic condition of the eyelids (blepharitis) and conjunctiva. This condition can interfere significantly with quality of lite because of constant eye itchiness and in severe cases there is potential impairment of visual function. Subcategories of allergic conjunctivitis are a) Seasonal and perennial allergies (IgE-mediated allergies), b) Atopic keratoconjunctivitis (associated with atopic eczema), c) Vernal keratoconjunctivitis (a subset of immune disorders, 50% IgE related), d) Contact blepharoconjunctivitis (similar to contact dermatitis, e.g., use of eye makeup) and e) Giant papillary conjunctivitis (associated with use contact lenses). Conjunctivitis can occur without an allergic etiology (e.g., exposure to chemical irritants). A common denominator of symptoms is ocular itch.

Atopic dermatitis (eczema) is an inflammatory disease of the skin. All parts of the skin may become itchy and inflamed. Lesions, including scratch lesions, are usually conspicuous on the flexures of the elbows and knees, possibly because these areas sweat more. Many atopic dermatitis patients also have allergic rhinitis and asthma. Symptoms are more frequent in children and young adults than adults. Recently, two new medications have been approved by the US FDA for atopic dermatitis: dupilumab (a monoclonal antibody) and crisaborole (an ointment). Both medications have a slow onset of therapeutic action of >6 weeks. Dupilumab is very expensive for an one year treatment. The efficacy of crisaborole is modest and it is a greasy ointment that is not favored by atopic patients. A side-effect of dupilumab in eczema patients is blepharitis which can be relieved with DIPA administered with an eye wipe.

Cholestatic Itch. In certain systemic disorders, such as cholestasis, renal failure and kidney dialysis, liver failure, and lymphoma, there are blood borne pruritogens that cause generalized itching. The exact chemical identities of these pruritogens are not well established, but are likely to be bile acids in the case of liver disease and kidney dialysis patients. The itching is intense and causes much hardship in the patients. During pregnancy some subjects also develop cholestatic itching which is intense and for which no medical treatment is known. The itch is not accompanied by skin inflammation.

Dermatological disorders are diseases of the skin, nails or hair. The skin has three layers; the epidermis, dermis and subcutaneous layer. The epdidermis includes the keratinized stratum corneum. The eyelids, cornea, tongue and parts of the buccal cavity are keratinized and thus considered as skin. The body's internal surfaces, the mucous membranes, do not have a keratin layer. The skin is the largest organ of the body, but the epidermis is only about 1 mm thick. The epidermis is densely infiltrated with nerve endings. The epidermal turnover time, that is, the time to replace itself, is about 1.5 months. Inflammation can occur from all three skin layers, but itch primarily originates from the epidermis. Approximately 80% of patients visiting a dermatology specialist complain of itch (J. Rinaldi. The itch-scratch cycle. Dermatology, Practical and Conceptual 9: 90-97, 2019).

Dermatome. In the body, the area innervated by a single spinal nerve is a called a dermatome. Inputs from immediately adjacent dermatomes can influence the sensations from one locale because there is overlap in the somatotopic organization of sensory projections. This overlap of sensory inputs is called convergence. A good example of convergent mechanisms in antinociception is itch and scratching. Mechanoreceptors are activated by scratching to reduce itch, but it is not necessary to precisely scratch the point source of the itch. Adjacent sites will suffice.

DIPA compounds DIPA is the abbreviation for 1-[Diisopropyl-phosphinoyl]-alkane. The third alkyl group in the molecule may be described by a number: hence, 4, 5, 6, 7, 8, 9, and 10 correspond to the butyl, pentyl, hexyl, heptyl, octyl, nonyl, and decanyl side chain, respectively. These alkanes are linear or "normal [n]" in configuration, with the phosphinoyl group attached to the primary, or "1-"position, of the carbon chain in the third sidechain. These compounds are also known as trialkylphosphine oxides or 1-dialkylphosphorylalkanes.

Dysesthesia. Injury to the surface of the body activates nerve endings that transmit signals interpreted by the brain as "discomfort" or "dysesthesia" (not feeling right). Examples of dysesthesia are soreness, irritation, itch, burning sensations, and pain. Dysesthesia is a general term that describes discomfort and is more inclusive than words such as "pain" or "itch." Dysesthetic sensations are conspicuous when epithelia and transitional epithelia are chronically injured.

Itch-scratch cycle Scratching relieves an itch, but a vicious itch-scratch cycle can cause more damage to the skin, perpetuate inflammation, and lead to excoriations and to disfiguring lichenification. The itch-scratch cycle is a well-known phenomenon in childhood and canine atopy where shields are put up to prevent the subject from scratching at the sites of inflammation and itch. Itch prevents a good night's sleep and an atopic dermatitis patient will scratch themselves vigorously even when asleep. An effective medication should prevent itch within minutes after application and act sufficiently long to allow the subject to go to sleep. The subject should be instructed to apply the medication after washing, to use on an as-needed basis, and to apply at night before sleep, because scratching can take place after the subject is asleep. This is especially important for children. The medication should also put a break on the itch-scratch cycle and thus promote healing.

Post-Burn Pruritus. During the recovery phase after a burn injury, the healing skin becomes intensely itch. Clinically, post-burn pruritus tends to be intractable to conventional treatment. Preliminary studies indicate that a DIPA-1-7 gel is effective for the relief of post-burn pruritus.

Receptive field of a sensory neuron is the region in space in which a stimulus will modify the firing of the neuron. The receptive field is spatially determined by the distribution of the nerve endings of the neuron. For the epithelium, the nerve endings are interdigitated with the cell layers at the basal layer of the epithelium. A receptive field, even though smaller than a $mm^2$, when activated by the appropriate stimulus, e.g. nociceptive or pruritic, can totally dominate the attention of the brain and mind. Witness what happens when a sharp pin or sting comes into contact with skin or when a dog is pre-occupied with a flea bite.

Scalp Itch. The sensory information from the scalp, e.g. from the crown or occiput, is conveyed by branches of the trigeminal nerve and from cervical nerves (V1: ophthalmic division of trigeminal nerve; V2: maxillary division of the trigeminal nerve; V3: mandibular division of the trigeminal nerve; C2: second cervical nerve; C3: third cervical nerve). The bulbs of hair follicles on the scalp have a dense innervation. Seborrheic dermatitis is an inflammatory condition caused in part by fungal infection. It can occur on the scalp and cause dandruff and itch. Psoriais is another common cause of scalp itch, especially on the hairline.

TRP channels. The transient receptor potential (TRP) family of cation channels are peripheral detectors of temperature and nociceptive and painful stimuli. These receptors on sensory neurons respond to stimulation by activating nerve action potentials that are transduced in sensations. The TRPM8 receptor signals heat abstraction. TRP signals allow the organism to detect, react, and adjust to external irritants.

Urticaria also known as hives is a disease characterized by the sudden onset of "wheals" (areas of red skin, with raised and itchy bumps) on any parts of the body. The wheals can be quite large and alarming, but are not life-threatening. The triggers are usually allergy to a food item, such as seafood, but there are multiple triggers. The skin layer is intact, but it is the release of histamine from mast cells in the epidermis and dermis that is causes the wheal and itch. The condition is treatable with oral antihistamines and in more severe cases with oral prednisone or Ig-E antibodies, but onset of drug effect takes about 12 hours. Urticaria is a recurrent condition and in some patients may persist for more than 6 weeks (chronic urticaria). The itching skin and cosmetic disfigurement of the red wheals are annoying features of urticaria.

Vulvar Anatomy and Itch. The female genitalia comprises the vulva with its outer and inner 'lips' called the labia majora and labia minora respectively and accessory structures which include the urethra, vestibule and vagina. The perineum is the area extending from beneath the vulva to the anus. The anogenitalia is innervated by the pudendal nerve which transmits pain messages and other sensations from the vulva. The pudendal nerve originates from the sacral spine, passes through the pelvis and enters the vulvar region from the hip bone. Braches of the pudendal nerve include the inferior rectal nerve, perineal nerve and dorsal nerve of the clitoris. These nerves provide sensory information and control urination, defecation and orgasm. Vulvar itch is a common condition seen in the clinic with multiple causes. This subject has been reviewed (Raef H S, Elmariah S B. Vulvar Pruritus: A Review of Clinical Associations, Pathophysiology and Therapeutic Management. Front Med. 2021; 8(April):1-10) and the information incorporated herein by reference (In males, the penis is the source of itch). Injury and inflammation to the anogenitalia surfaces and structures give rise to the dysesthesia of vulvar itch and pain, and frequently occurs because of allergies, immune disorders, infections, hormonal imbalance, or trauma. Vulvodynia and dyspaurenia are dysesthesias that can occur in the absence of anatomic evidence of tissue damage. Lichen sclerosus is an inflammatory condition that affects the surfaces of the anogenitalia and causes severe itch.

DIPA Compounds

The DIPA compounds of the present discovery are achiral and are examples of 1-di-alkyl-phosphinoyl-alkanes [(O═)$PR_1R_2R_3$] wherein each of $R_1$, $R_2$, and $R_3$ is an alkyl group, and in particular where $R_1$ and $R_2$ are isopropyl, and $R_3$ is a linear alkyl group of 5 to 9 carbons, and which have the following general formula of Formula 1:

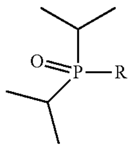

Formula 1: wherein R=n-pentyl, n-hexyl, n-heptyl, n-octyl, or n-nonyl

TABLE 2

| DIPA compounds | | | |
|---|---|---|---|
| Code | Chemical Name | Formula/ Weight | Chemical Structure |
| DIPA-1-5 | 1-di-isopropyl-phosphinoyl-pentane | $C_{11}H_{25}OP$ 204.32 | 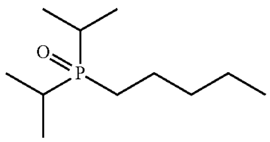 |
| DIPA-1-6 | 1-di-isopropyl-phosphinoyl-hexane | $C_{12}H_{27}OP$ 218.32 | 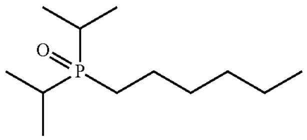 |
| DIPA-1-7 | 1-di-isopropyl-phosphinoyl-heptane | $C_{13}H_{29}OP$ 232.34 | 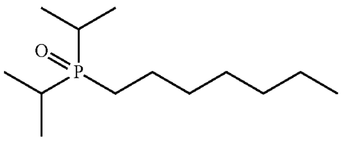 |
| DIPA-1-8 | 1-di-isopropyl-phosphinoyl-octane | $C_{14}H_{31}OP$ 246.37 | 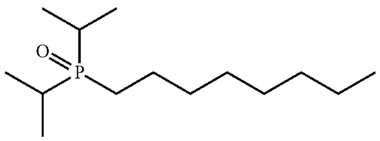 [SMILES: CCCCCCCCP(=O)(C(C)C)C(C)C] |
| DIPA-1-9 | 1-di-isopropyl-phosphinoyl-nonane | $C_{15}H_{33}OP$ 260.40 | 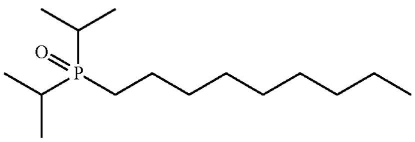 [SMILES: CCCCCCCCCP(=O)(C(C)C)C(C)C] |

Chemical Synthesis

The DIPA compounds were prepared by the following general method: 100 mL (23.7 g, ~200 mmol) of isopropylmagnesium chloride (or sec-butylmagnesium chloride in the case of the di-sec-butyl derivatives) were obtained from Acros, as a 25% solution in tetrahydrofuran (THF) and placed under nitrogen in a 500 mL flask (with a stir bar). Diethylphosphite solution in THF (from Aldrich, D99234; 8.25 g, 60.6 mmol in 50 mL) was added drop-wise. After approximately 30 minutes, the reaction mixture warmed up to boiling. The reaction mixture was stirred for an extra 30 minutes, followed by a drop-wise addition of the appropriate n-alkyl iodide solution in THF (from TCl; 60 mmol in 20 mL). The reactive mixture was then stirred overnight at room temperature. The reaction mixture was diluted with water, transferred to a separatory funnel, acidified with acetic acid (~10 mL), and extracted twice with ether. The ether layer was washed with water and evaporated (RotaVap Buchi, bath temperature 40° C.). The light brown oil was distilled under high vacuum. The final products, verified by mass as determined by mass spectrometry, were transparent liquids that were colorless. Synthesis was conducted by professional chemists at Phoenix Pharmaceuticals, Inc. (Burlingame, California), Uetikon Laboratories (Lahr, Germany) and Dong Wha Pharmaceuticals (Seoul, Korea). Table 2 compounds are embodiments of the invention. The following compounds (Table 3) were also prepared by this general synthetic method and used for comparisons.

TABLE 3

Chemical structures of test compounds.

| Code | Chemical Name | Chemical Structure |
|---|---|---|
| 2-4 | 1-di(sec-butyl)-phosphinoyl-Butane | 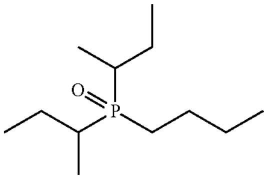 |
| 2-5 | 1-di(sec-butyl)-phosphinoyl-Pentane | 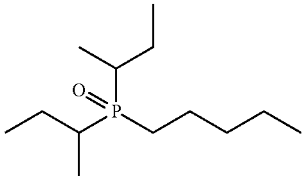 |
| 2-6 | 1-di(sec-butyl)-phosphinoyl-Hexane | 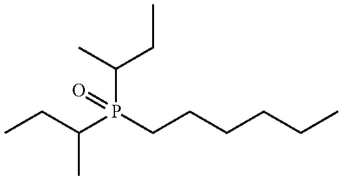 [SMILES: CCCCCCP(=O)(C(C)CC)C(C)CC] |
| 2-7 | 1-di(sec-butyl)-phosphinoyl-Heptane | 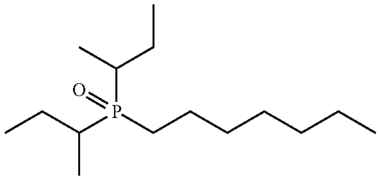 [SMILES: CCCCCCCP(=O)(C(C)CC)C(C)CC] |
| 2-8 | 1 di(sec butyl) phosphinoyl Octane | 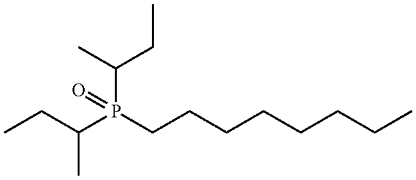 [SMILES: CCCCCCCCP(=O)(C(C)CC)C(C)CC] |
| 3-1 | 1-di(iso-butyl)-phosphinoyl-Pentane | 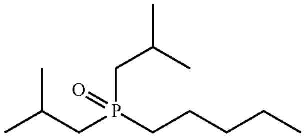 |
| 3-2 | 1-di(sec-butyl)-phosphinoyl-3-methyl-butane | 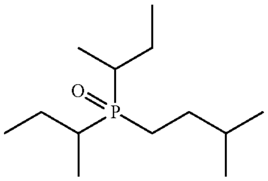 |
| 3,4-6 | 1-isopropyl-sec-butyl-phosphinoyl-hexane | 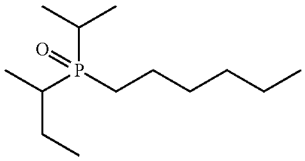 |

TABLE 3-continued

| Chemical structures of test compounds. | | |
|---|---|---|
| Code | Chemical Name | Chemical Structure |
| 3,4-7 | 1-isopropyl-sec-butyl-phosphinoyl-heptane | 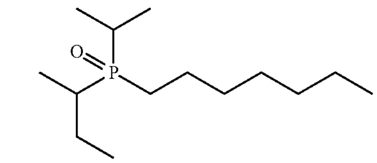 [SMILES: CCCCCCCP(=O)(C(C)C)C(C)CC] |
| 3,4-8 | 1-isopropyl-sec-butyl-phosphinoyl-octane | 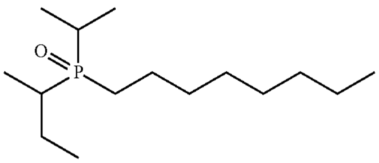 [SMILES: CCCCCCCCP(=O)(C(C)C)C(C)CC] |
| 3,4-9 | 1-isopropyl-sec-butyl-phosphinoyl-nonane | 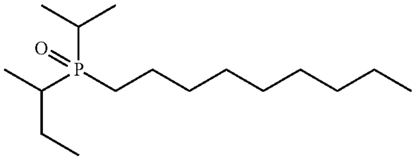 [SMILES: CCCCCCCCCP(=O)(C(C)C)C(C)CC] |

The 3,4-X series are "mixed" isopropyl-sec-butyl compounds (Table 3). These were synthesized by Dr. Jae Kyun Lim of Dong Wha Pharmaceuticals, using the method described below. Briefly, as illustrated in the following scheme, triethyl phosphite (A) was reacted with sec-butyl magnesium bromide (B) and then hydrolysed with dilute hydrochloric acid to give the mono-alkyl compound (C). The product (C) was then reacted isopropyl magnesium bromide (D) to give the di-alkyl compound (E), which was then reacted with a suitable alkyl iodide (F) to give the target trialkyl phosphine (G).

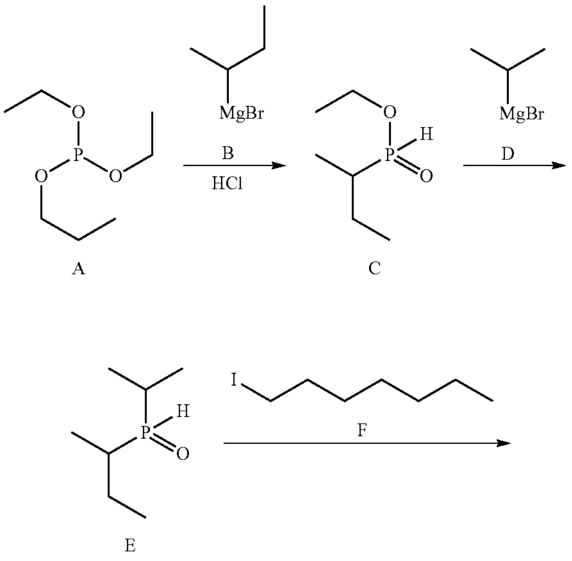

-continued

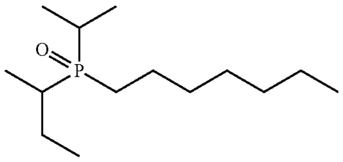

G

General Observations of Unusual Properties

DIPA compounds are colorless liquids with a density less than water. The preferred embodiments DIPA-1-7, DIPA-1-8 and DIPA-1-9 exert an icy sensation that can modulate skin dysesthesia caused, for example, by various dermatitis (e.g. atopic or urticarial) and on mucous membranes (esp. DIPA-1-8 and DIPA-1-9). Similar structures were described by Rowsell and Spring U.S. Pat. No. 4,070,496 (1978) ~40+ years ago but have remained dormant in the scientific literature. The '496 structures (Table 1) all have their "head" (phosphine oxide group) covered by larger, more lipophilic groups. The applicant noted that '496 did not include the di-isopropyl analogs. The applicant synthesized these analogs (which are achiral, by contrast to the structures of '496 which are >95% chiral). The applicant found that, by minimizing the two alkyl side chains to di-isopropyl, the "head" of the prototypical molecule now is more polar (hydrophilic) and more miscible in the polar environment of water. This increased water-solublility is striking (Table 4). The water solubility of the DIPA if at least 10× greater than the di-sec-butyl or the mixed isopropyl-sec-butyl analogs. The DIPA analogs are now mobile in the extracellular fluids and permeate between cells to access nerve endings in the stratum basale.

TABLE 4

Water solubility (mg/ml) of 1-dialkylphosphorylalkanes ($R_1R_2R_3P{=}O$).

| No. Carbons | 13 | | 14 | | 15 | | 16 | |
|---|---|---|---|---|---|---|---|---|
| $R_1$, $R_2$ | $R_3$ | | $R_3$ | | $R_3$ | | $R_3$ | |
| di-sec-butyl- | pentane | 22 | hexane | 8 | heptane | <3 | octane | <3 |
| isopropyl-sec-butyl- | hexane | 25 | heptane | 20 | octane | <3 | nonane | <3 |
| di-isopropyl- | heptane | >300 | octane | >300 | nonane | >300 | decane | <3 |

When DIPA compounds are applied to the facial skin as an aqueous solution at 1-10 mg/mL or a 1% hydrogel there is little irritation. For certain analogs, contacting the periorbital or zygomatic skin with a solution at a concentration of 1-10 mg/mL produce a sensation of "dynamic cool" that is felt within one minute after application. A single application can evoke this "energizing" sensation, which can counteract fatigue for several hours. DIPA-1-7, especially, has intense dynamic cooling.

Periorbital administration of DIPA and related di-secbutyl analogs will leave a residue on the eyelid skin. When the eyelids become wet, for example, by taking a shower or sweating, the residual compound will wash onto the cornea and cause stinging and irritation. This will limit the choice of the compound for applications wherein delivery is to the eyelid skin such as in blepharitis and conjunctivitis. Among the compounds of Formula 1, DIPA-1-8 and DIPA-1-9 have minimal residual irritation, and so are especially useful for the longer term treatment of ocular dysesthesia. The efficacy of DIPA-1-9 in the treatment of patients with the "dry eyes syndrome" is demonstrated in Case Study 7. DIPA-1-7 is more useful for application wherein the sensory effect is immediate and energizing. Both DIPA-1-7 and DIPA-1-8 are useful for treatment of skin dysesthesia (e.g., skin irritation, itchy skin, or painful skin). DIPA-1-8 is slightly longer-acting than DIPA-1-7.

Compositions. One aspect of the present discovery pertains to a composition (e.g., a pharmaceutical composition) comprising a DIPA compound, as described herein, and a pharmaceutically acceptable carrier, diluent, or excipient. Another aspect of the present discovery pertains to a method of preparing a composition (e.g., a pharmaceutical composition) comprising mixing a DIPA compound, as described herein, and a pharmaceutically acceptable carrier, diluent, or excipient.

In one embodiment, the composition comprises the DIPA compound at a concentration of 0.005-2.0% wt/vol. In one embodiment, the composition is a liquid or semi-liquid composition (lotion, cream, or ointment), and comprises the DIPA compound at a concentration of 0.5-20 mg/mL. In one embodiment, the composition is a liquid composition, and comprises the DIPA compound at a concentration of 1-5 mg/mL. In one embodiment, the composition is a liquid composition, and comprises the DIPA compound at a concentration of 5-10 mg/mL. In one embodiment, the composition is a liquid composition, and comprises the DIPA compound at a concentration of 10-20 mg/mL. The composition may be provided with suitable packaging and/or in a suitable container. For example, the composition may be provided as a swab, wipe, pad, or towellette (e.g., suitably sealed in a wrap) carrying a DIPA compound or a composition comprising a DIPA compound. Similarly, the composition may be provided as a patch, e.g., a controlled-release patch, e.g., suitable for application to the skin, e.g., the skin above the supraclavicular fossa or the steronomastoid muscle. Similarly, the composition may be provided as an aerosolized spray delivered from a pressurized container. Similarly, the composition may be provided in a manually-activated sprayer (e.g., with a suitable small orifice) linked to a reservoir containing a DIPA compound or a composition comprising a DIPA compound, for example, capable of delivering an unit volume (e.g., of 0.05 to 0.15 mL), for example, to the skin surface.

Use in the Manufacture of Medicaments. Another aspect of the present discovery pertains to use of a DIPA compound, as described herein, in the manufacture of a medicament, for example, for use in a method of treatment, for example, for use a method of treatment of a disorder (e.g., a disease) as described herein. In one embodiment, the medicament comprises the DIPA compound.

Methods of Treatment. Another aspect of the present discovery pertains to a method of treatment, for example, a method of treatment of a disorder (e.g., a disease) as described herein, comprising administering to a subject in need of treatment a therapeutically-effective amount of a DIPA compound, as described herein, preferably in the form of a pharmaceutical composition.

Disorders Treated. In one embodiment (e.g., of use in methods of therapy, of use in the manufacture of medicaments, of methods of treatment), the treatment is treatment of: sensory discomfort (e.g., caused by irritation, itch, or pain); a skin dysesthesia; atopic dermatitis; contact dermatitis; prurigo nodularis; urticaria; milaria rubra; lichen sclerosus; anogenital skin inflammation; acne; acneiform eruptions; pruritus of the elderly, pruritus from cholestasis and liver disease; pruritus from lymphoma; pruritus from kidney failure dialysis; seborrheic dermatitis; psoriasis; rosacea; ocular pain and discomfort; and itch from the healing of burn wound.

The term "sensory discomfort", as used herein, relates to irritation, itch, pain, or other dysesthesias (abnormal sensations; such as burning sensations, or feeling the presence of a foreign body, or pins and needles) from the body surfaces. The term implies activation of nociceptors located on sensory nerve endings of the body. Nociceptors are stimulated, for example, by high temperatures, mechanical pressure, chemicals (e.g., capsaicin, acidity, pollutants, etc.), injury, inflammation, and inflammatory mediators. A DIPA compound, such as DIPA-1-7 or DIPA-1-8, that decreases sensory discomfort, can be termed an anti-nociceptive agent.

In one embodiment, the sensory discomfort is irritation, itch, or pain. In one embodiment, the sensory discomfort is caused by a skin dysesthesia. In one embodiment, the skin dysesthesia is skin irritation, itchy skin, or painful skin. In one embodiment, the sensory discomfort is caused by atopic dermatitis. In one embodiment, the sensory discomfort is caused by canine atopic dermatitis. In one embodiment, the treatment is treatment of a skin dysesthesia. In one embodiment, the treatment is treatment of dermatitis. In one embodiment, the treatment is treatment of atopic dermatitis. In one embodiment, the treatment is treatment of canine atopic dermatitis. In one embodiment, the treatment is treatment of contact dermatitis. In one embodiment, the treatment is treatment of urticaria. In one embodiment, the treatment is treatment of the pruritus of the elderly. In one embodiment, the treatment is treatment of the pruritus of milaria rubra. In one embodiment, the treatment is treatment of the pruritus of liver disease (cholestasis). In one embodiment, the treatment is treatment of the pruritus of patients on kidney dialysis. In one embodiment, the treatment is treatment of the pruritus of patients with lymphoma. In one embodiment, the treatment is treatment of the dysesthesia of psoriasis. In one embodiment, the treatment is treatment of the dysesthesia of neurogenic/neuropathic itch. In one embodiment, the treatment is treatment of the dysesthesia of lichen sclerosus. In one embodiment, the treatment is treatment of ocular discomfort. In one embodiment, the ocular discomfort is caused by eye strain; eye fatigue; eye surgery; an airborne irritant or pollutant that interacts with the eye surface; extended wear of contact lenses; excessive exposure to the sun; conjunctivitis; conjunctivitis in atopic dermatitis patients treated with dupilumab; or the dry eyes syndrome. In one embodiment, the treatment is treatment of milaria rubra. In one embodiment, the treatment is treatment is to convey a sense of refreshment to the skin in a human or a mammal.

Treatment. The term "treatment," as used herein in the context of treating a disorder, pertains generally to treatment of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment." The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies. The term "treatment" includes combination treatments and therapies, in which two or more treatments or therapies are combined, for example, sequentially or simultaneously. For example, the compounds described herein may also be used in combination therapies, e.g., in conjunction with other agents. One aspect of the present discovery pertains to a DIPA compound as described herein, in combination with one or more (e.g., 1, 2, 3, 4, etc.) additional therapeutic agents. The particular combination would be at the discretion of the physician or the pharmacist who would select dosages using his common general knowledge and dosing regimens known to a skilled practitioner. Examples of additional therapeutic agents include: an anti-inflammatory glucocorticosteroid; an analgesic; a sympathomimetic amine decongestant; an anti-histamine; a local anesthetic; an ophthalmic lubricant or cleanser; a sunscreen ingredient; an anti-acne agent; a keratolytic agent; an anti-hemorrhoidal agent; an agent for vulvar itch or discomfort; an antibiotic; a skin moisturizer; or an anti-skin ageing agent.

Routes of Administration. The DIPA compound or pharmaceutical composition comprising the DIPA compound may suitably be administered to a subject topically, for example, as described herein. The term "topical application", as used herein, refers to delivery onto surfaces of the body in contact with air, which includes the skin, the anogenital surfaces, the transitional epithelial surfaces of the orbit, the lips, the tip of the nose, and the anus. Particularly preferred sites of application are the surfaces innervated by the trigeminal and cervical and sacral nerves which include the scalp, facial skin, periorbital skin, and lips, and the surfaces of the neck, elbows and knees, which are frequently associated with the pruritus of atopic eczema and psoriasis. Yet another preferred site is the scalp, which can be a site of inflammation in psoriasis and seborrheic dermatitis.

In one embodiment (e.g., of use in methods of therapy, of use in the manufacture of medicaments, of methods of treatment), the treatment is treatment by topical administration. In one embodiment, the treatment is treatment by topical administration to skin. In one embodiment, the treatment is treatment by topical administration to facial skin. In one embodiment, the treatment is treatment by topical administration to periorbital skin, eyelid skin, zygomatic skin, malar skin, forehead skin, or scalp. In one embodiment, the treatment is treatment by topical administration to skin surface of the orbit, frontal bone, or zygomatic. In one embodiment, the treatment is treatment by topical administration to skin surface of the anus and/or the male or female genitalia. In one embodiment, the treatment is treatment by topical administration to skin above the flexure of the limbs, the supraclavicular fossa or the steronomastoid muscle.

Subject/Patient. The subject/patient may be a mammal, for example, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human. In one preferred embodiment, the subject/patient is a human.

Formulations. While it is possible for a DIPA compound to be administered alone in a liquid, for example, dissolved in saline or water, it may also be prepared as a pharmaceutical formulation (e.g., composition, preparation, medicament) comprising at least one DIPA compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilizers, solubilizers, surfactants (e.g., wetting agents), masking agents, and coloring agents. The formulation may further comprise other active agents. Thus, the present discovery further provides pharmaceutical compositions, as described above, and methods of making pharmaceutical compositions, as described above. If formulated as discrete units (e.g., swab, wipe, pads, towellettes, gels, lotion, cream, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation. Suitable carriers, diluents, excipients, etc. can be found in standard pharmaceutical texts, for example, Remington's Pharmaceutical Sciences, 23rd edition, Mack Publishing Company, Easton, Pa., 2020; and Handbook of Pharmaceutical Excipients, 9th edition, 2018.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary. Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols. Additionally, the DIPA compound may be used as an adjunct in a pharmaceutical formulation or cosmetic formulation.

Dosage. It will be appreciated by one of skill in the art that appropriate dosages of the DIPA compounds, and compositions comprising the DIPA compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular DIPA compound, the route of administration, the time of administration, the duration of the treatment, other drugs, compounds, and/or materials used in combination, the severity of the disorder, and the species, sex, age, weight, condition, general health, and prior medical history of the patient. The amount of DIPA compound and route of administration will ultimately be at the discretion of the physician, pharmacist, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

Targets for Delivery. Epithelial cells line surfaces and cavities of organs throughout the body. When there are two or more layers of epithelia, it is called stratified epithelium. Historically, stratified epithelia were divided into two broad categories: keratinized stratified epithelia, and non-keratinized stratified epithelia. Keratinized epithelium, such as the epidermis of the skin, has an exterior layer of dead cells [stratum corneum] composed of keratin proteins that are tough and water-impermeable. By contrast, non-keratinizing stratified epithelia are located on "soft tissues" of the body such as the lining of the nasal and throat cavities and the oesophageal surface. Keratinizing tissues withstand injury better than non-keratinizing tissues. Non-keratinizing epithelial surfaces must be kept moist by glandular (serous and mucous) secretions in order to avoid desiccation.

The stratum corneum (keratinized layer of dead cells) is a formidable barrier to drug penetration to neuronal receptive fields embedded in epithelial tissues underneath the keratin. The barrier thickness and the layers of dead cells vary. The heel and palm have the most dead cell layers (~82 layers). The genitalia (e.g. penile shaft) and eyelids have fewer layers (4 to 8 layers). The skin of the face has about 10 to 14 layers, and the torso has about 12 to 16. The limbs have somewhat more layers (~15+). Dermatitis occurs frequently occur on the extremities (e.g. elbow and knee flexures in atopic dermatitis) and on the trunk and scalp for psoriasis. Hand eczema frequently occurs on the hand (contact dermatitis). Urticaria can occur all over the body, the wheals appearing on the torso, neck and buttocks.

However, the stratum corneum is not a solid brick and mortar wall, but has water pores, like limestone, through which water soluble molecules may pass between cells and through cells. The intracellular water transport channels on keratinocytes are called aquaporins (Patel R et al. Aquaporins in the Skin. Adv Exp Med Biol. 2017; 969:173-191). The active ingredient must reach the nerve endings, which are located in the basal layer of the skin (stratum basale). A surprising finding here was the ability of DIPA compounds to inhibit dysesthesia when applied as a water solution on a wipe. The likely explanation is that the DIPA is passing between cells through water channels, and not across cells. The current topical antinociceptive (pain-suppressant) compounds that have efficacy on sensory discomfort of keratinized skin are high concentrations of I-menthol (36% alcoholic solution) or a local anesthetic gel. But these two types of topical medications have problems of greasy feel and irritation, and of hypersensitivity reactions.

The targets for topical delivery of the DIPA compounds are located on the nerve endings of the receptive fields of peripheral and cranial sensory nerves. For the face, the receptive fields of the ophthalmic and maxillary branches of the trigeminal nerve are the preferred target sites.

Figure 2:
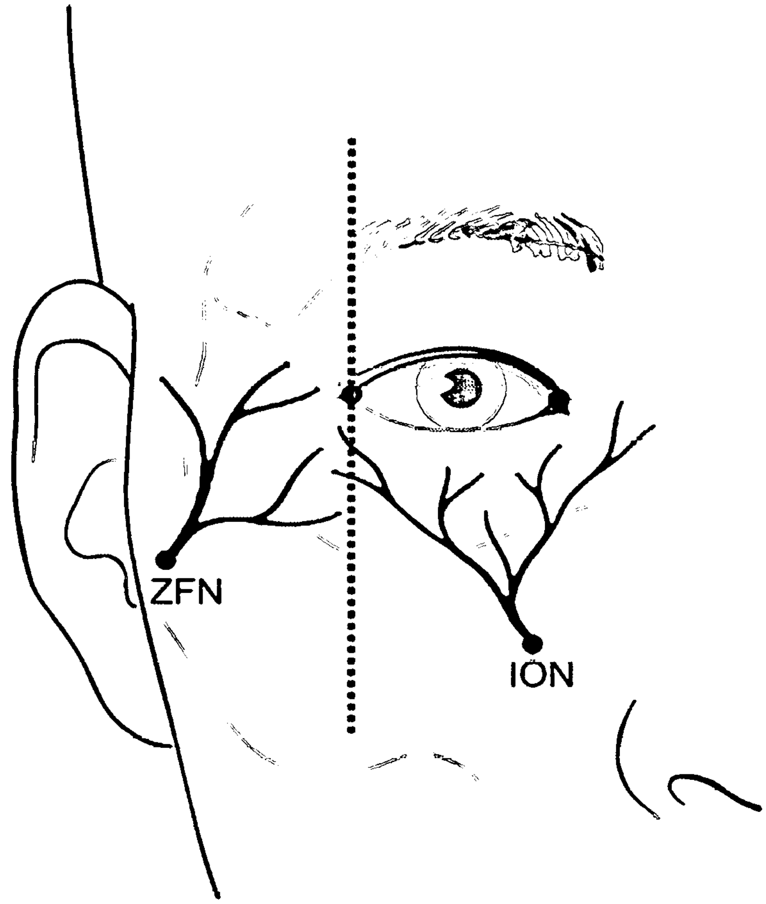
FIG. 2. is an illustration of the human face showing the innervation of the cheekbone skin by the zygomatic facial nerve (ZFN) and the infraorbital nerve (ION). The receptive fields of these nerve endings were used for testing compounds applied to the cheekbone skin. Diagram adapted from Hwang et al. [Cutaneous innervation of the lower eyelid. J. Craniofacial Surgery 19: 1675-1677, 2008].

FIG. 2. is an illustration of the human face showing the innervation of the cheekbone skin by the zygomatic facial nerve (ZFN) and the infraorbital nerve (ION). The receptive fields of these nerve endings were used for testing compounds applied to the cheekbone skin. Diagram adapted from Hwang et al. [Cutaneous innervation of the lower eyelid. J. Craniofacial Surgery 19: 1675-1677, 2008].

In these studies, the primary site of testing was the zygomatic (cheekbone) skin. Alternatively, if the cooling agent is to be used vulva for itch it may also be applied to the skin above the labia with a spray. The cooling agent may be directly applied to the sites of injury and/or inflammation. Secondary sites are the skin over the frontal bone and the scalp, but higher concentrations of cooling agent are required for these sites. In practice, the cooling agent can be sprayed or applied (e.g., with a swab or pad or within a gel, lotion, cream or ointment) over the skin of the orbit, the cheekbone (zygomatic), or on the skin beneath the eye, between the cheekbone and nose. For this site, the receptive fields are from the sub-divisions of the trigeminal nerve, namely, the zygomaticfacial nerve of the maxillary nerve (V2) and the supraorbital and supratrochlear branches of the frontal nerve (V1).

Methods of Delivery. The delivery of the DIPA compounds can be achieved with the compound dissolved in a liquid vehicle, e.g., in water or saline, or a solution, a hydrogel, a lotion, on a swab, wet wipe, or as an aerosolized mist in a solid or semi-solid vehicle, e.g., a cream or an ointment. Gels are semisolid, jelly-like formulations with varying degrees of viscosity. A gel forms a solid three-dimensional network that spans the volume of a liquid medium. Gels are made with gelling agents that cross-link or associate with a liquid phase. Examples of gelling agents are: cellulose derivatives [methylcellulose, carboxymethyl-cellulose, hydroxylpropylcellulose; carbomers [carbopol®910, carbopol®941]; poloxamers [Pluronic®, Tween]; carbomer polymers, and natural polymers such as tragacanth, acacia, gelatin, sodium alginate, alginic acid, and xanthan gum. A single-phase system is a gelling agent plus an active ingredient that dissolves [in water] without visible particles and looks clear. A topical gel optimally liquefies when in contact with skin or mucous membranes. The compounds of Formula 1 are attractive for delivery as gels because they dissolve in water and form a one-phase system at therapeutic concentrations. The methods for formulating topical gels are well-known to the art and extensively described in such sites in Lubrizol.com [a company that manufactures ingredients for cosmetics, personal care, skin care, and eye care]. A preferred concentration of the DIPA compound is 0.01 to 2.0% wt/vol. Unless otherwise stated, wt/vol is measured in units of $g/cm^3$ or g/mL and so 0.01% wt/vol is obtained from 0.1 mg (0.0001 g) DIPA compound in 1 $cm^3$ of composition; and 2% wt/vol is obtained from 20 mg (0.02 g) DIPA compound in 1 $cm^3$ of composition.

For a liquid vehicle, a preferred single delivered volume is 0.02 to 0.15 mL. Such a volume, delivered for example as a lotion or a wipe, does not cause much residual liquid at the delivery site, as the liquid is absorbed. For a liquid vehicle, a preferred concentration of the DIPA compound is in the range of 0.5 to 30 mg/mL. For the orbit, a preferred concentration is 1 to 5 mg/mL. For the zygomatic and infraorbital skin, a preferred concentration is 5 to 10 mg/mL. For the forehead skin and scalp, a preferred concentration is 10 to 30 mg/mL. A preferred amount of the DIPA compound delivered at the site of application is 0.01 to 5 mg; for example, 0.1 to 5 mg.

Wiping of the DIPA compound on the target skin can be done with pre-medicated wipes, which are well-known in personal care products, for example, to wipe a baby's skin after a diaper change, or to remove make-up on the face (e.g., Pond's 6"×8" (15 cm×20 cm) Clean Sweep Cleansing and Make-up Remover Towelettes). Usually, these wipes are packaged as a single-use sealed unit or in a multi-unit dispenser. For single units, suitable wrapper materials are those which are relatively vapor impermeable, to prevent drying out of the wipe, and able to form a "peelable" seal. Examples of suitable wipe materials for practicing this discovery include polyamide (20% Nylon)-polyester, rayon (70%)-polyester (30%) formed fabric, polypropylene non-woven, polyethylene terephthalate (PET), polyester poly-propylene blends, cotton, viscose, rayon, or microfibers (synthetic fibers that measure less than one denier or one decitex).

Alternatively, a solution containing a DIPA compound may be supplied in a reservoir bottle with individual applicators, or as a pre-packaged individual unit. For example, Puritan 803-PCL applicators are ideal cotton-tipped applicators attached to a 3-inch (~7.5 cm) polystyrene rod for delivery of a DIPA compound onto the periorbital skin. Examples of how such applicators can be individually packaged are the SwabDose™ from Unicep Corporation (1702 Industrial Drive, Sandpoint, Idaho, USA), and the Pro-Swabs from American Empire Manufacturing (3828 Hawthorne Court, Waukegan, Illinois, USA). Each applicator tip is saturated by dipping the absorbent material of the tip (e.g., 40 to 100 mg of cotton) in 0.1 to 1.5 mL of an aqueous solution of a DIPA compound and packaged in an individual container.

For application to the face, the individual is instructed to gently apply the cream, lotion, gel, or wet wipe onto, or to spray, to the target facial skin with the eyelids shut, or other skin surface(s). The instructions for application may include teaching the individual to repeat application, or "topping up", to ensure that sufficient composition is delivered to the target. Once the subject has learned what to expect, the individual can adjust the dosage (e.g., by dabbing at the medial or lateral edges of the orbit), as needed, to achieve the desired effect. It has been observed that individuals quickly learn how to effectively apply the cooling agent after one or two trials.

For application to the anogenital skin or other highly sensitive surfaces, the DIPA compound may be wiped or sprayed, for example, to deliver volumes of approximately 0.15 mL per unit. Alternatively, a dropper may be used together with a wipe with an soft material such as 100% cotton.

Mechanisms of Action The sensory neurons express receptors and ion channels on their membranes to detect various stimuli. Stimuli are converted by the receptor to electrical signals which are transmitted to the central nervous system (spinal cord or brain) and become a sensation. These sensory receptors are transducers and the process is called transduction.

DIPA compounds applied topically relieve skin discomfort by evoking a sense of "dynamic cool" at sites of application. The feeling is of robust freshness, as if suddenly a fresh, cool breeze was blown on the skin (e.g., on the face) or cold water was splashed onto the skin. This effect with DIPA-1-7 is especially intense. This transduction process, receptor mechanisms, and the significance of dynamic cooling for anti-pruritic actions are further discussed herein, and called "cool esthesia."

Neurophysiology: Small myelinated (Aδ) and unmyelinated fibers (C fibers) increase afferent firing rate when skin temperature is lowered, for example, between 25° C. to 10° C. These neuronal signals that detect heat abstraction are transmitted to the central nervous system and generate conscious perception of coolness and cold. When skin temperature is raised from 35° C. and 40° C., firing rates are increased in C fibers and these fibers signal warmth [Hutchinson et al. Quantitative analysis of orofacial thermoreceptive neurons in the superficial medullary dorsal horn of the rat. J. Neurophysiol. 77, 3252-66, 1997]. The receptive mechanisms and "cable lines" for cool/cold and warm are separate and distinct, but reciprocally inhibit each other in the brain and perhaps also in the periphery. The sensory receptors are modality specific and do not respond to mechanical stimulation. At the molecular level, the target binding sites for cooling agents are thought to be located on TRP ion channel receptors that depolarize in response to a drop in temperature. Heat abstraction decreases the threshold for discharge of the receptor, and the facilitated depolarization initiates the axonal responses that create the neuronal signal.

The central response of these cool-sensing neurons has been recorded from rat superficial medullar dorsal horn that responds to innocuous thermal stimulation of the rat's face and tongue [Hutchinson et al., 1997]. Step changes of $-\Delta 5°$ C. stimulate cells with both static firing rates and cells that have dynamic properties [Davies et al. Sensory processing in a thermal afferent pathway. J. Neurophysiol. 53: 429-434, 1985]. Similar studies in cats and humans showed that step decreases in temperatures (dynamic changes), as low as Δ0.5° C./second, were readily detectable by neurons and by psychophysical measurements [Davies et al. Facial sensitivity to rates of temperature change: neurophysiological and psychophysical evidence from cats and humans. J. Physiol. 344: 161-175, 1983]. From a study of the spike patterns of neuronal discharge (impulses/second), it was clear that dynamic, and not static firing responses to a change in temperature were the most powerful stimuli for generating coolness/cold sensations That is, the brain "sees" −Δ° C./t and not absolute ° C. Thus, a cooling agent that simulates −Δ° C./t on nerve discharge will produce "dynamic cooling".

Dynamic Cooling to Treat Skin Dysesthesia and Pruritus. Dynamic cooling (versus static cooling/cold) is essential for a robust sensory effect. For example, if one is tired and driving a vehicle, turning on the air-conditioning and blasting the air onto the face will counteract fatigue [dynamic cooling]. But just turning on the air conditioner to lower ambient temperature and being chilled inside the vehicle [static cooling] will not make much of a difference. The benefits of the topical sensory therapy are illustrated by the Case Studies described herein.

Receptor Mechanisms: There is consensus that "TRP-" ion channel receptors (e.g., A1, M8, and V1 to 4) are the principal elements for physiological temperature detection. The TRPM8 receptor is the one that responds to sensory/cooling agents such as menthol and icilin [McKemy et al. Identification of a cold receptor reveals a general role for TRP channels in thermosensation, Nature, 416, 52-58, 2002]. TRPM8 is a protein with 1104-amino acid residues and has six transmembrane domains. Activation of this receptor by lowering ambient temperature results in opening of pores of transmembrane loops and non-specific cation entry into the cell. Depolarization of TRPM8 receptors on sensory neurons then transmit signals primarily via Aδ (and some C) fibres to the spinal cord or brain.

While this concept for the role of TRPM8 in sensory physiology may be valid for physical changes in temperature, the interpretation of the sensory effects of chemical agents such as menthol and icilin are more complex. Menthol not only stimulates TRPM8 in vitro, but also TRPV3, a receptor associated with warmth and glycinergic transmission, and other TRP receptors [Macpherson et al. More than cool: promiscuous relationships of menthol and other sensory compounds. Mol Cell Neurosci 32:335-343, 2006: Sherkheli et al., Supercooling agent icilin blocks a warmth-sensing ion channel TRPV3, Scientific World Journal, 2012; Cho et al. TRPA1-like channels enhance glycinergic transmission in medullary dorsal horn neurons. J Neurochem 122:691-701, 2012]. Thus, menthol and icilin are multivalent "promiscuous" cooling agents and their sensory effects may not be associated with any one particular receptor protein. A laboratory reagent specific and selective for TRPM8 will be valuable for experiment.

The applicant has screened a large database of cooling agents but, surprisingly, only found the DIPA compounds to produce super-robust dynamic cooling on skin. DIPA-1-8 and DIPA-1-9 produces strong cooling and its actions are prolonged, but it does not quite have the super "wow" cooling effects of DIPA-1-6 and DIPA-1-7. Other categories of cooling agents, such as p-menthane carboxamides, generally have shorter durations of action and less dynamic cool, and thus are less suitable for the uses contemplated herein. Thus, the DIPA compounds, by contrast to menthol, p-menthane carboxamides, and icilin, are ideal selective reagents on TRPM8 function.

Based on what is know about TRPM8 physiology, it is logical to assume that DIPA-1-7, DIPA-1-8, and DIPA-1-9 bind to an allosteric site on a voltage-gated ion channel receptor located on a nerve ending that is sensitive to a decrement in physical temperature. This binding event facilitates neuronal depolarization to a cooling/cold signal, and an action potential is transmitted via Aδ and C fibers towards the central nervous system. If the nerve ending is located on the facial skin, the signal is recordable in animals from dorsal surface of the trigeminal nucleus in the brainstem, such as in the studies of Hutchison et al., vide supra. Subsequent rostral transmission and integration of signals give rise to the perception of coolness/cold and its topographical association with the site of stimulation.

When one examines the structure-activity relationships (SAR) of the DIPA compounds, it is noted that when $R_1$=$R_2$=isopropyl and $R_3$=$C_6$ to $C_9$, then cooling is observed. Strong cooling of long duration is obtained with $R_3$=n-octyl ($C_9$). Refreshing cooling of long duration is obtained with $R_3$=n-nonyl ($C_9$). The special attribute of the n-nonyl analog is the absence of any burning/tingling sensations, even at high concentrations of 5% in water. By contrast, the sec-butyl containing analogs are less potent. As shown in the studies described herein, this distinction between di-sec-butyl and di-iso-propyl compounds is also seen in animal studies on shaking behavior, an indicator of cooling actions in the rat. Fur-coated animals shake like a dog because the trigger events are a cool and wet stimuli. The shaking is inhibited by heat. The wet-dog shaking behavior assay is manifested as a rapid alternating contraction of the supination and pronation muscles about the spinal axis can be readily observed and counted. All fur-coated and feathered animals—when wet and cold—shake, like a wet dog [Dickerson et al., Wet mammals shake at tuned frequencies to dry. J. Royal Society, Interface 9, 3208-3218, 2012; Ortega-Jimenez, V. M. et al. Aerial shaking performance of wet Anna's hummingbirds. J. Royal Society, Interface 9, 1093-9, 2012; Wei, Pharmacological aspects of shaking behavior produced by TRH, AG-3-5, and morphine withdrawal, Federation Proc. 40: 1491-1496, 1981].

"Wet-dog shaking" has been studied in detail in animals. Rats can shake their head, the upper torso, or the shaking can be sufficiently violent to affect the whole body and make the animal lose its balance. DIPA-1-7 and DIPA-1-8 elicit the vigorous type of shaking. The purpose or survival value of shaking to fur-coated and feathered organisms is to remove water droplets trapped on or near the skin. Removal of the water droplets reduces the organism's need to expend energy to remove the water by evaporation. The likely equivalent behaviour to shaking in humans is shivering, a condition caused by generalized sensations of coolness/cold. Human subjects recovering from the deep hypothermia of anesthesia manifest vigorous shaking; a condition called post-anaesthetic shivering. Human subjects can also do a "wet shake" by deliberate effort when coming out of a swimming pool.

Icilin (1-[2-hydroxy]-4-[3-nitrophenyl]-1,2,3,6-tetrahydropyrimidine-2-one) induces vigorous shaking in rats [Wei. Chemical stimulants of shaking behavior. J. Pharmacy and Pharmacology 28: 722-724, 1976], Surprisingly, two potent p-menthane carboxamide cooling agents [(R)-2-[((1R,2S,5R)-2-isopropyl-5-methyl-cyclohexanecarbonyl)-amino]-propionic acid ethyl ester, and [((1R,2S,5R)-2-isopropyl-5-methyl-cyclohexanecarbonyl)-amino]-acetic acid isopropyl ester], which have $EC_{50}$ values similar to icilin at the TRPM8 receptor, do not evoke shaking (when injected at 50 mg/kg s.c. in male rats and observed for 1 hour. Icilin activation at the TRPM8 receptor is abrogated by a G805A mutation at the second to third transmembrane loop, but the effects of menthol are not affected. It is likely that DIPA-1-6, DIPA-1-7, and DIPA-1-8 also have specific sites of binding and activation on the TRPM8 receptor which are not shared by menthol or p-menthane carboxamides. Studies by Wei and Kuhn have shown that DIPA-1-6 and DIPA-1-7 are still active on TRPM8 receptors with the G805A mutation.

Watson et al., 1978 [New compounds with the menthol cooling effect. J. Soc. Cosmet. Chem. 29: 185-200,1978] showed that a polar oxygen moiety capable of hydrogen bonding is an essential structural requirement for bioactivity. A Hückel molecular orbital calculation (using Molecular Modelling Pro v6.0.3, ChemSW Inc, Fairfield, CA 94534, USA) on the isopropyl analogs versus the sec-butyl analogues favours a slightly higher partial negative charge (0.007e) on the oxygen in the sec-butyl entities, suggesting that the sec-butyl substituents facilitate a higher affinity of the oxygen to the hydrogen binding site of the receptor. Thus it is possible that isopropyl, with a "looser" affinity can associate and disassociate with the receptor more rapidly, favoring the generation of a dynamic onset and offset response of the receptor. This rapid interaction with the binding site will favour a more "dynamic" and intense stimulation of cooling and give rise to the phenomenon known as shaking.

TRPM8, TRPA1, and TRPV1 Receptor Assays TRPM8 is a cation channel activated by cold temperatures and cooling compounds such as menthol and icilin. In this application, the in vitro effects of test compounds were evaluated on cloned hTRPM8 channel (encoded by the human TRPM8 gene, expressed in CHO cells) using a Fluo-8 calcium kit and a Fluorescence Imaging Plate Reader (FLIPRTETRA™) instrument. To examine the specificity of the test compounds, further tests were conducted on TRPV1 channels (human TRPV1 gene expressed in HEK293 cells) and TRPA1 channels (human TRPA1 gene expressed in CHO cells). The assays were conducted by ChanTest Corporation, 14656 Neo Parkway, Cleveland, OH 44128, USA. Cells, grown in culture, were seeded at an approximate density of 30,000 cells/well overnight, and loaded for ~1 hr with 2 M Fura-2 (Molecular Probes, Leiden, The Netherlands), and then placed on glass coverslips. Test solutions were added with a micropipette positioned close to the cells. Emission intensity from cells was measured for 90 sec, at every 4 or 5 sec, using excitation wavelengths of 340 and 380 nm and an emission of 520 nm. Fluorescence emission intensity ratios at 340 nm/380 nm excitation (R, in individual cells) were recorded with a FlexStation and the ImageMaster suite of software (PTI, South Brunswick, NJ). Samples were tested in triplicate at each concentration and the averaged values analyzed by non-linear regression using an a sigmoidal function fit of the points to obtain an estimated EC50 (median effective concentration) (GraphPad Prism software, La Jolla, California). The assays in vitro provide information of relative potency and selectivity at the receptor. The DIPA are selective for TRPM8 and do not activate TRPV1 or TRPA1.

Selection of Active Ingredient. Ideally, an active pharmaceutical ingredient (API) formulated for delivery to the keratinized skin should be stable, non-toxic, and sufficiently long-acting and potent to activate the mechanisms that result in an antinociceptive effect. The API should be miscible in a composition so that during manufacture the formulation maintains a constant concentration. The final product should meet standards of purity, cleanliness and sterility. For purposes of formulation, the API can be a liquid at standard conditions of temperature and pressure (STP) and that is evenly dissolved in aqueous solutions at neutral pH and/or isotonicity. Sterility of the final product can be optimally achieved by using purified reagents and filtration through micropore filters, heating, or irradiation. Standard excipients, such as emulsifying agents, isotonic saline, solvents, stabilizing agents, and preservatives, may be added to optimize the formulations, but the important ingredients should be preferably soluble in aqueous media such as purified water or a standard dermatological solvent.

For a given individual, the perceived sensation is a function of the particular cooling agent, the dose, the vehicle used to carry the cooling agent, the method of topical delivery, and the nature of the target surfaces. The applicant has screened compounds such as icilin and p-menthane carboxamides, on the facial skin (Wei. Sensory/cooling agents for skin discomfort. Journal Skin Barrier Research 14: 5-12, 2012). The studies here identify DIPA compounds as having the preferred desired properties of an ideal API for dysesthesia and itch. To summarize, the design concepts for choosing a particular DIPA are:

- The definition of a rationale for using a "dynamic cool" sensation on skin to relieve sensory discomfort and a description of the neurophysiology and receptor mechanisms of this action. This sensory effect in unusual and only found in certain DIPA compounds.
- Devising a delivery method for the ideal compound to its receptive field which exploits the water solubility of these analogs, thus reducing the need for excipients.
- Finding an ideal compound by experiment: DIPA-1-7, DIPA-1-8, and DIPA-1-9 are water-soluble (a clear solution is obtained at up to 20 mg/mL in distilled water), stable to heat, and may exert a "robust cool" sensation for up to five to seven hours at an applied concentration of 1 to 10 mg/mL. Tachyphylaxis does not develop to repeat applications. DIPA-1-7 is more like to produce icy cold when compared to DIPA-1-9.
- Defining the receptor targets of these compounds in vitro, and conducting experiments to show the selectivity of the chosen DIPA.
- Defining an animal model (e.g., "wet-dog shakes") that will illustrate the "dynamic cool" properties and allow further study of mechanisms of action and the selective differentiation of various analogs.
- Conducting tests in human volunteers that show efficacy of the DIPA compounds for reducing skin dysesthesia caused by various dermatological disorders.
- Conducting tests in human volunteers that show DIPA compounds, especially DIPA-1-7, are effective for relieving dysesthesia of the skin, and thus allowing use as an anti-nociceptive or anti-pruritic agent to treat dermatological disorders.

Examples of Applications of DIPA Compounds

The DIPA compounds, when applied to keratinized skin, have cooling effects that mimic heat abstraction, but without a change in tissue temperatures. These compounds, penetrate the skin barrier, reach nerve endings in the epidermis and dermis, and enter the systemic circulation to exert cooling actions. These effects are obtained at small volumes, e.g., 0.1 to 0.5 mL, applied at a concentration of 1 to 20 mg/mL, or 0.1 to 2% wt/vol. The onset of effect is rapid, less than 5 minutes, and the sense of coolness is robust, refreshing, and strong. Compounds with similar bioactivity on the skin are not currently known or used in cosmetic or therapeutic applications. A number of new applications are possible with DIPA having such unusual properties. And this is illustrated by use of DIPA in various dermatological disorders.

Dermatitis and Pruritus: Topical applications of DIPA produce cooling sensations. In the presence of dysesthesia and itch, these analogs exert anti-itch and other anti-nociceptive effects. As shown in the Case Studies described herein, various formulations potently stopped itching and discomfort. A most surprising recent event was the discovery that DIPA act on intact skin to stop itch. This is shown in patients with urticaria, cholestatic itch, and scalp itch. The DIPA-1-7 was also effective against milaria rubra (prickly heat), and against a recalcitrant case of prurigo nodularis (a form of chronic atopic dermatitis). No known topical medications that work quickly against these conditions. Data are also shown wherein DIPA is effective against blepharitis, conjunctivitis, and ocular pain. On the anogenital surfaces, DIPA is effective for lichen sclerosus and vulvar itch. The relief of itch and dysesthesia usually occur within 5 min after DIPA and lasts for several hours, a duration that is clinically significant.

A topical medication that relieves skin dysesthesia and itch has many applications in patients with dermatological disorders (~80% of whom complain of itch and skin irritation) including:

a) alleviation of irritation, itch and pain from dermatitis (atopic dermatitis, contact dermatitis, and irritant dermatitis, various forms of eczema);
b) itch and discomfort from skin infections, insect bites, sunburn, photodynamic treatment of skin (e.g., actinic keratoses, basal cell carcinoma), lichen sclerosus;
c) pruritus due to xerosis [especially dry skin itch of the elderly], psoriasis, or seborrheic dermatitis;
d) pruritus ani, hemorrhoidal discomfort, pain from anal fissures, pain or itch from anal fistulas, pain from hemorrhoidectomy, perineal inflammation, anogenital skin inflammation and discomfort due to various local causes such as incontinence, diaper rashes, prickly heat rash, and perineal inflammation;
e) pain from burned, traumatized, diseased, anoxic, or irritated skin (e.g., skin damaged by laser surgery, diabetic ulcers, sunburn, radiation), and from procedures related to wound debridement and wound healing;
f) stomatitis, cheilitis, itching of the lips from cold sores or gingivitis;
g) vulval pruritus and pain (e.g., from candidiasis or idiopathic, such as vulva vestibulitis and vulvodynia), dyspareunia, anogenital infections, including warts and sexually transmitted diseases, fungal infections, viral infections of the skin (especially in immunocompromised patients);
h) conjunctivitis, blepharitis, ocular surface irritation, pain from trauma and corneal abrasions, and pain from eye surgery.

Of special interest, is the use of DIPA-1-7 and DIPA-1-8 for scalp itch, e.g., in seborrheic dermatitis and psoriasis; these end-points being unmet medical needs. DIPA-1-7 may also be used to refresh the skin before application, or after removal of, cosmetics from the skin, to reduce the irritant effects of benzyoyl peroxide in the treatment of acne, and to reduce sebum secretion and the appearance of an "oily" skin.

Breaking the Itch-Scratch Cycle. Itch is the sensation that causes the desire or reflex to scratch. Itch can be quite intense, and evokes obsessive behavior. For example, I have seen a golfing friend scratch his ankles until it bled because of itch caused by insect bites (midges and sand flies). Scratching may have survival value because it rids fur-coated animals of parasites and insects on skin, but for humans excessive scratching exacerbates skin damage in dermatological disorders. Scratching injures skin and the injury provokes more itch and scratching, a phenomenon called the "itch-scratch cycle". MacDonald et al. has proposed a mechanism by which the itch-scratch cycle exacerbates tissue injury (Acta Dermato-Venereologica 97 (8): 1010, 2017). He stated that double-stranded RNA released from injured keratinocytes stimulates TOLL-3 receptors to generate more cytokines and chemokines, and thus inflammation is enhanced and perpetuated.

An anti-itch molecule may therefore not only provide symptomatic relief but also have a more subtle disease-modifying therapeutic effect in disorders such as atopic dermatitis wherein itch is localized and the itch-scratch cycle is a vicious contributor to the pathology of excoriations and lichenification. The irritated skin thickens and becomes chronically inflamed and fragile because of scratching, and is likely to breakdown with more scratching and rubbing. The ability to add a break to scratching is not restricted only to atopic dermatitis but also applicable to other dermatological disorders such as seborrheic dermatitis, acne or acneiform eruptions. Here, for example, the acne lesion is an inflammatory disorder of the sebaceous glands in the skin, and the subject picks and squeezes the lesions constantly. The mechanical damage to the inflamed skin aggravates the underlying tissue reactions. If a break can be applied to the tissue manipulation, then the lesion is given time to heal more quickly.

Itch prevents a good night's sleep and an atopic dermatitis patient will scratch themselves vigorously even when asleep. An effective medication should prevent itch within minutes after application and act sufficiently long to allow the subject to go to sleep. The subject should be instructed to apply the medication after washing, to use on an as-needed basis, and to apply thoroughly at night at sites of itch before sleep. This is especially important for children because the desire to scratch is instinctive and automatic, but will also damage the skin.

Pharmaceutical Adjunct: In pharmaceuticals or cosmeceuticals, the term "adjunct" is an additional substance, treatment, or procedure used for increasing the efficacy or safety of the primary substance, treatment, or procedure or for facilitating its performance. The DIPA compounds relieve sensory discomfort of the skin, have anti-nociceptive activity, and are active at less than 1 minute after application. They are ideal adjuncts for pharmaceuticals and for cosmetics applied to the skin.

An adjunct such as DIPA-1-7 may be used to increase the "apparent" efficacy of another primary ingredient, and thereby improve patient satisfaction and adherence to a dosage schedule. For example, DIPA-1-7 at about 0.5 to 2%, stops itching within minutes after application. If combined with an anti-inflammatory steroid, the preparation may be more desirable than the anti-inflammatory steroid alone, which takes longer to act. Anti-inflammatory steroids, such as hydrocortisone, triamcinolone, and clobetasol are used for sensory discomfort of the skin in disorders such as insect stings, contact dermatitis, atopic eczema, and psoriasis. The presence of DIPA-1-7 as an adjunct, in addition to helping to stop the itch, may help reduce the dose or the frequency of application of the primary ingredient, yet achieve an equivalent therapeutic effect. This adjunct benefit will be especially beneficial in the use of skin steroids because of the well-known undesirable effects of collagen degradation, tissue thinning, and increased susceptibility to infections. An adjunct that reduces dosage or promote greater efficacy of the primary ingredient has value. Other primary anti-pruritics are aluminum acetate, and strontium chloride or strontium nitrate.

For skin disorders, compositions of the present discovery may also be used as adjuncts for procedures such as phototherapy, laser therapy, cryotherapy, or UV-therapy of the skin. Pharmaceuticals that may be used, in combination or in sequence with adjunct DIPA compounds include anti-inflammatory steroidal agents, anti-inflammatory analgesic agents, antihistamines, sympathomimetic amine vasoconstrictors, local anesthetics, antibiotics, anti-acne agents, topical retinoids, drug for genital warts and skin cancer, drugs for wrinkles and ageing skin, anti-hemorrhoidal agents, drugs for vulvar itch, drugs to stimulate hypertrichosis, skin moisturizers, and agents for keratolysis.

Examples of steroidal anti-inflammatory agents include hydrocortisone, clobetasol, clobetasol propionate, halobetasol, prednisolone, dexamethasone, triamcinolone acetonide, fluocinolone acetonide, fluocinonide, hydrocortisone acetate, prednisolone acetate, methylprednisolone, dexamethasone acetate, betamethasone, betamethasone valerate, flumetasone, fluticasone, fluorometholone, beclomethasone dipropionate, etc. Examples of anti-inflammatory analgesic agents include methyl salicylate, monoglycol salicylate, aspirin, indomethacin, diclofenac, ibuprofen, ketoprofen, naproxen, pranoprofen, fenoprofen, sulindac, fenclofenac, clidanac, flurbiprofen, fentiazac, bufexamac, piroxicam, pentazocine, etc. Examples of antihistamines include azelastine hydrochloride, diphenhydramine hydrochloride, diphenhydramine salicylate, diphenhydramine, chlorpheniramine maleate, promethazine hydrochloride, etc. Examples of sympathomimetic amine vasoconstrictors include phenylephrine hydrochloride, oxymetazoline, naphazoline, and other imidazoline receptor agonists used for nasal decongestant activity and for redness and vasodilatation on the ocular surfaces. Examples of skin moisturizer ingredients include the three categories of humectants, emollients and preservatives. Humectants, such as urea, glycerin and alpha hydroxy acids, help absorb moisture from the air and hold it in the skin. Emollients, such as lanolin, mineral oil and petrolatum, help fill in spaces between skin cells, lubricating and smoothing the skin. Preservatives help prevent bacteria growth in moisturizers. Other ingredients that moisturizers may contain include vitamins, minerals, plant extracts and fragrances. Example of an agent for hypertrichosis is bimatoprost.

Study 1

Toxicity Studies. Preliminary toxicological studies were conducted on DIPA 1-7. It was not mutagenic in the Ames test (Strains TA 98 and TA100, with and without liver activation) (tests conducted by Apredica, Watertown, MA, USA). DIPA-1-7, dissolved in 3% ethanol/97% 1,2-propanediol, or vehicle alone, was administered at 20 mg/kg perioral for 7 days (n=10 per group) to male rats, and on the 8$^{th}$ day, the animals were euthanized with sodium pentobarbital and the major organs (body, heart, liver, lungs, kidney, testes, brain) were removed and weighed. Heart tissues (ventricle and heart valves) and liver samples were stained with hematoxylin and eosin and the histology examined. There was no significant difference in body or organ weights between the two groups and the heart and liver histology were normal.

Study 2

Tissue Temperature. The compounds of the present discovery cool but do not alter tissue temperatures. The average forehead skin temperature of subjects (N=5) was measured following application of DIPA-1-7 (with a wipe at a concentration of 20 mg/mL in distilled water) to the forehead skin. The results are summarized in Table 5. The subjects noted the cooling effect of DIPA-1-7 on the skin which lasted for 30-45 minutes; however, skin temperatures were not affected.

TABLE 5

Skin temperatures of human forehead after DIPA-1-7, 20 mg/mL.

| | Temperature (° C.) | |
|---|---|---|
| Time | Control | DIPA-1-7 |
| Before | 37.3 | 37.4 |
| 0 minutes | 37.2 | 37.4 |
| 15 minutes | 37.5 | 37.5 |
| 30 minutes | 37.1 | 37.1 |
| 45 minutes | 37.4 | 37.2 |
| 60 minutes | 37.0 | 37.1 |

Study 3

Effects of Compounds on Facial Skin. When a test compound is applied to the skin, the resulting sensations may be characterized. The quality of the sensations produced by individual compounds favors certain characteristics that are distinct. The sensations evoked, their descriptors, and their proposed mechanism of action, are summarized in Table 6. For any compound, there may be some overlap in activity, but usually one compound occupies only one or two categories of effect. For example, icilin is exclusively cool, with very little "cold". DIPA-1-6 and DIPA-1-7 are exceptional in producing pleasant, robust "dynamic cool." DIPA-1-8 and DIPA-1-9 are strong cold-producing agents.

TABLE 6

Descriptor and proposed mechanisms of DIPA compounds on skin.

| Type of Sensation | Descriptor | Proposed Mechanisms on Sensory Neurons |
|---|---|---|
| Inactive | No effect | — |
| Cool, steady and pleasant | Cool | Balanced stimulation of static and dynamic |
| Cold, constant, but limited by desensitization | Cold | Higher stimulation of static |
| Dynamic cooling, robust cool/cold, strong refreshing | Dynamic cool | Higher stimulation of dynamic |
| Stinging cold, sometimes with irritation | Icy cold | Stimulation of dynamic and static, and also nociceptive sites |

In the studies described herein, the sensation of coolness/cold is rated as 0, 1, 2, or 3 with: 0 as no change; 1 as slight coolness, or cold; 2 as clear-cut signal of coolness or cold; and 3 as strong cooling or cold. The sensations are recorded at intervals of 5 to 15 minutes, until at least two successive zeroes are obtained. The onset of drug action is taken as the time to reach 2 units of coolness intensity.

The duration of sensory action is defined as the offset time minus the onset time. The offset of drug action is defined here as the time when coolness intensity drops below 2, after previously surpassing 2 units. An inactive compound is defined as one that does not exceed 2 units of cooling for 5 minutes or more after application. The offset endpoint is sometimes unstable for compounds that act for two or more hours, because the coolness/cold sensation may fluctuate due to environmental variables such as sunlight, ventilation, activity, and the "reservoir effect." For example, DIPA-1-8 and 2-8 are exceptionally long-acting on the skin.

The effects of test compounds on facial skin were determined. Compounds were tested on the cheekbone skin (zygomatic). Test compounds were applied using cotton gauze (0.4 g, rectangular, 50 mm×60 mm; from CS-being, Daisan Cotton, Japan). The test compounds were used at a concentration of 20 mg/mL in distilled water. The onset and duration of the sensory effect was measured with a stopwatch. The degree of "dynamic cool" was graded from 0 to +++, with intermediate steps of + and ++. An anti-fatigue effect was present only if there was sufficient "dynamic cool." The results are summarized in Table 7.

TABLE 7

Sensory effects after application to zygomatic and forehead skin.

| Code | $R_3$ | Carbon atoms | Onset (min) | Sensory Quality | Anti-Fatigue | Duration (hr) | Reservoir Effect |
|---|---|---|---|---|---|---|---|
| DIPA-1-5 | 5 | 11 | ~1 | dynamic | 0 | 0.5 | No |
| DIPA-1-6 | 6 | 12 | ~1 | dynamic | ++ | 1.3 | Yes |
| DIPA-1-7 | 7 | 13 | ~1 | dynamic-icy | +++ | 3.2 | Yes |
| DIPA-1-8 | 8 | 14 | ~1 | cold-icy | ++ | 4.0 | Yes |
| DIPA-1-9 | 9 | 15 | ~2 | cool | 0 | 2.0 | No |
| 2-4 | 4 | 12 | ~1 | cool | 0 | 0.3 | No |
| 2-5 | 5 | 13 | ~1 | cool | 0 | 1.1 | Yes |
| 2-6 | 6 | 14 | ~2 | cold | + | 1.5 | Yes |
| 2-7 | 7 | 15 | ~2 | cold | + | 2.4 | Yes |
| 2-8 | 8 | 16 | 5 | cold | 0 | 5.6 | Yes |

Each of 3-1 and 3-2 was also tested and found to be inactive on periorbital, and zygomatic/forehead skin.

For further comparisons, the newly synthesized "mixed" 1-isopropyl-sec-butyl-phosphorylalkanes (3,4-6, 3,4-7, 3,4-8 and 3,4-9) were tested on zygomatic skin (FIG. 2). The test procedures were modified because of the limited quantities of these analogs. To deliver the solution to the skin, a 80%-polyester-20%-viscose rayon wipe was cut into squares (7×8 cm, 0.45 g each) and a precise volume (2.5 mL) of test solution is added to the wipe using a dropper bottle. Delivery and scoring of effect. An average 74±2 μL volume containing the test ingredient was wiped onto the receptive fields of the nerves on the zygomatic process (cheek-bone). As before, the sensory effects of cool/cold were recorded at 5 and 10 min intervals. Quarter and half point scores are allowed. Scoring is stopped when two zeroes are observed in a 10 min interval. At least four trials are conducted for each concentration with two to three volunteer test subjects for each compound. The result from the testing of DIPA-1-8 at three concentrations is shown in FIG. 3.

Figure 3:
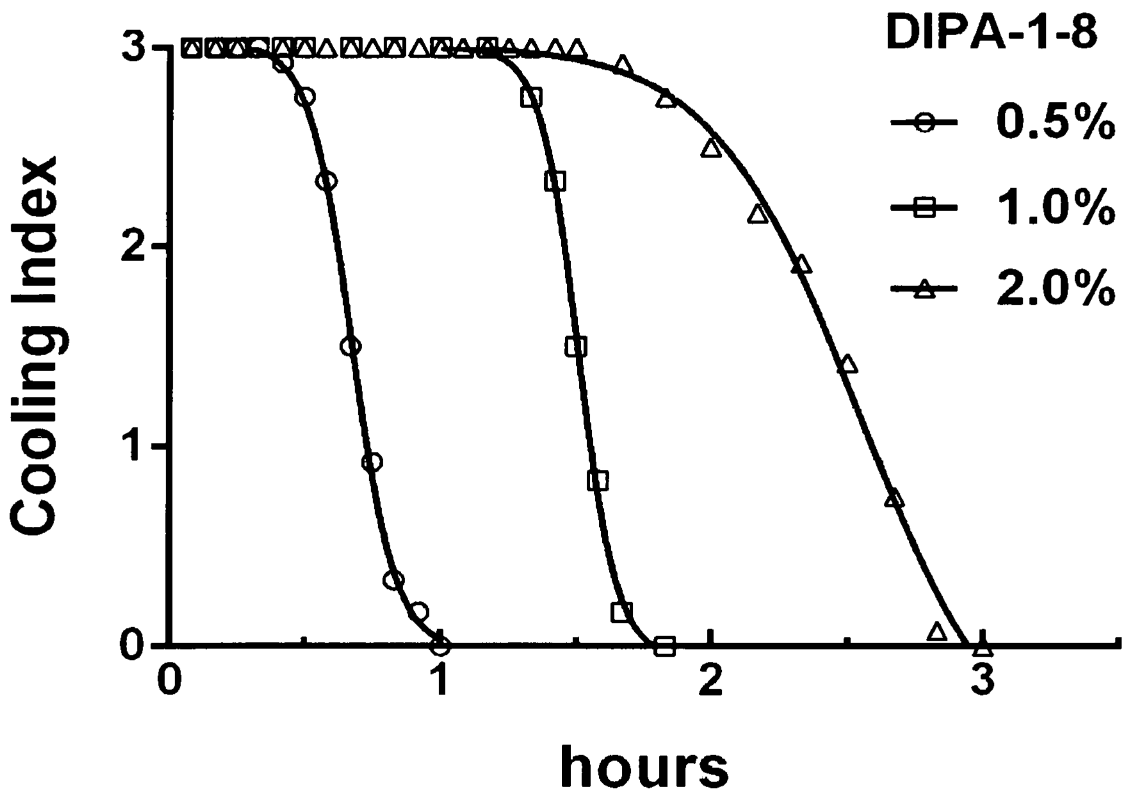
FIG. 3. shows the cooling sensations evoked by topical wiping of different concentrations of DIPA-1-8 onto the skin above the zygomatic process. The cooling activity can be measured as the intensity/duration area-under-curve (AUC) or as time for half maximal effect ($T_{-1/2}$), using software of the GraphPad Prism package. The graph shows the dose-response curve for the compound DIPA-1-8 applied at 0.5, 1 and 2% (5, 10, and 20 mg/mL dissolved in distilled water).

FIG. 3. shows the cooling sensations evoked by topical wiping of different concentrations of DIPA-1-8 onto the skin above the zygomatic process. The cooling activity can be measured as the intensity/duration area-under-curve (AUC) or as time for half maximal effect ($T_{-1/2}$), using software of the GraphPad Prism package. The graph shows the AUC dose-response curve for the compound DIPA-1-8 applied at 0.5, 1 and 2% (5, 10, and 20 mg/mL dissolved in distilled water).

Figure 4:
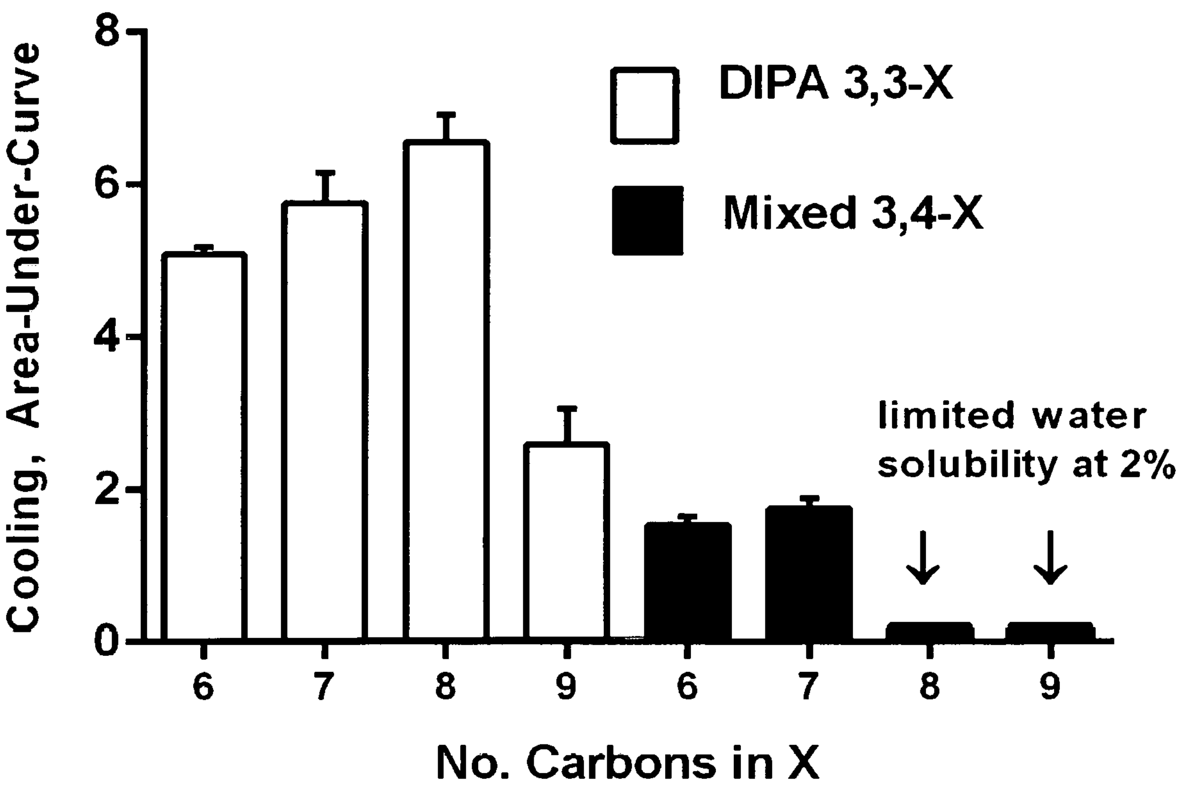
FIG. 4. shows the cooling sensations evoked by topical wiping of different compounds onto the skin above the zygomatic process. The cooling activity is expressed as the integrated intensity/duration area-under-curve (AUC), using software of the GraphPad Prism package. Test concentration was 2% (20 mg/mL in distilled water). The diisopropyl analogs are DIPA 3,3-X and isopropyl, sec-butyl analogs are Mixed 3,4-X. The "X" refers to the number of carbons on the third alkyl group. It can be seen that the Mixed analogs are much less active on the cheekbone skin than the corresponding diisopropyl analogs.

A comparison of the DIPA diisopropyl analogs (3,3-X) versus the mixed propyl-sec-butyl analogs (3,4-X) are shown in FIG. 4. Statistical significant differences (P<0.01) are seen between 3,3-x and the asymmetrical chiral 3,4-x analogs. The 3,4-8 and 3,4-9 formed a milky/small oil droplet emulsion at 20 mg/mL.

Notably, DIPA-1-7 selectively produced the unusual sensation of "dynamic cool" and also had anti-fatigue effects. From the data shown above, it can be seen that, among these compounds, DIPA-1-7 evoked "dynamic cool" on both periorbital and zygomatic/forehead surface. Another compound with similar properties was DIPA-1-8, but this compound was more cold/icy cold, although it had the desirable property of a longer duration of action on the zygomatic/forehead surface. The long duration of action of DIPA-1-7 and DIPA-1-8 on the skin adds value as an anti-itch agent. As shown in the case studies described below, a single application of DIPA-1-7 is sufficient to counteract itch.

A special value of DIPA-1-9 is the comfortable cooling it provides and its long duration of action after periorbital application, and the absence of any stinging. Thus, it has a special therapeutic niche for the relief of dyesthesia on transitional epithelia, especially for eyelids and conjunctiva. The selective attributes of DIPA-1-7 and DIPA-1-8 are unexpected, surprising, and has practical applications for dyesthesia.

Study 4

Agonist Activity of Compounds on TRPM8. The in vitro effects of a first set of test compounds (Table 8) were evaluated on cloned hTRPM8 channel (encoded by the human TRPM8 gene, expressed in CHO cells) using a Fluo-8 calcium kit and a Fluorescence Imaging Plate Reader (FLIPR$^{TETRA}$™) instrument. The assays were conducted by ChanTest Corp. (14656 Neo Parkway, Cleveland, OH 44128, USA).

Test compounds and positive control solutions were prepared by diluting stock solutions in a HEPES-buffered physiological saline (HBPS) solution. The test compound and control formulations were loaded in polypropylene or glass-lined 384-well plates, and placed into the FLIPR instrument (Molecular Devices Corporation, Union City, CA, USA). The test compounds were evaluated at 4 or 8 concentrations with n=4 replicates per determination. The positive control reference compound was L-menthol, a known TRPM8 agonist. The test cells were Chinese Hamster Ovary (CHO) cells stably transfected with human TRPM8 cDNAs.

For FLIPRTETRA™ assay, cells were plated in 384-well black wall, flat clear-bottom microtiter plates (Type: BD Biocoat Poly-D-Lysine Multiwell Cell Culture Plate) at approximately 30,000 cells per well. Cells were incubated at 37° C. overnight to reach a near confluent monolayer appropriate for use in a fluorescence assay. The test procedure was to remove the growth media and to add 40 μL of HBPS containing Fluo-8 for 30 minutes at 37° C. 10 μL of test compound, vehicle, or control solutions in HBPS were added to each well and read for 4 minutes. Concentration-response data were analyzed via the FLIPR Control software that is supplied with the FLIPR System (MDS-AT) and fitted to a Hill equation of the following form:

$$\text{RESPONSE} = \text{Base} + \frac{\text{Max} - \text{Base}}{1 + \left(\frac{xhalf}{x}\right)^{rate}}$$

where: "Base" is the response at low concentrations of test compound; "Max" is the maximum response at high concentrations; "xhalf" is the $EC_{50}$, the concentration of test compound producing half-maximal activation; and "rate" is the Hill coefficient. Nonlinear least squares fits were made assuming a simple one-to-one binding model. The 95% Confidence Interval was obtained using the GraphPad Prism 6 software.

The results are summarized in Table 8.

TABLE 8

$EC_{50}$ and relative potency of compounds on TRPM8.

| Code | $EC_{50}$ μM | 95% Confidence Interval | Relative Potency |
|---|---|---|---|
| Menthol | 3.8 | 2.5 to 5.6 | 1.0 |
| DIPA-1-5 | 5.6 | 4.4 to 7.2 | 0.7 |
| DIPA-1-6 | 2.4 | 1.5 to 4.0 | 1.6 |
| DIPA-1-7 | 0.7 | 0.5 to 1.0 | 5.4 |
| DIPA-1-8 | 0.7 | 0.5 to 1.0 | 5.4 |
| DIPA-1-9 | 0.9 | 0.4 to 2.5 | 4.0 |
| 2-4 | 14.5 | 7 to 29 | 0.3 |
| 2-5 | 1.7 | 1.0 to 2.9 | 2.2 |
| 2-6 | 0.8 | 0.5 to 1.3 | 4.7 |
| 2-7 | 1.1 | 0.6 to 2.3 | 3.4 |
| 2-8 | 1.3 | 0.7 to 2.3 | 2.9 |
| 3-1 | 24 | 8 to 76 | 0.2 |
| 3-2 | 4.2 | 1.6 to 10.8 | 0.9 |

Of the 12 compounds tested, all showed full efficacy on the TRPM8 receptor, i.e., at higher tested concentrations there was ~100% stimulation of calcium entry, and the data fitted a sigmoidal dose-response curve. The results for the "di-isopropyl" compounds of this invention are illustrated in FIG. 4. The $EC_{50}$ of the more potent compounds (DIPA-1-7, DIPA-1-8, DIPA-1-9, 2-5, 2-6, 2-7, 2-8) fell within a narrow range with overlapping 95% Confidence Intervals. The potency of DIPA-1-7, DIPA-1-8, and DIPA-1-9 are similar and significantly greater than the potencies of DIPA-1-5 and DIPA-1-6. By contrast the structural modifications of comparative compounds 3-1 and 3-2 resulted in a significant loss of bioactivity To examine the specificity of the test compounds, further studies were conducted on TRPV1 channels (human TRPV1 gene expressed in HEK293 cells) and TRPA1 channels (human TRPA1 gene expressed in CHO cells). The test cells were Chinese Hamster Ovary (CHO) cells or Human Embyronic Kidney (HEK) 293 cells transfected with human TRPV1 or TRPA1 cDNAs. The positive control reference compound was capsaicin (a known TRPV1 agonist) or mustard oil (a known TRPA1 agonist). DIPA-1-7 and DIPA-1-8 did not exhibit any agonist on antagonist activity on TRPA1 channels at maximum tested concentrations of 100 μM. A weak TRPV1 agonist activity was found for DIPA-1-7, but this was not dose-dependent.

In bioactivity studies, potency was not correlated to the TRPM8 $EC_{50}$. For example, DIPA-1-5 and DIPA-1-6 are more potent in producing shaking behavior than DIPA-1-7 and DIPA-1-8 [see Study 5]. There were no distinguishing features in the TRPM8 $EC_{50}$ data which enabled prediction of which compounds have potent "dynamic cool" properties in vivo.

Further tests were conducted on "mixed" isopropyl-sec-butylphosphorylhexane and heptane analogs. The data were collected by Andersson et al. of King's College, London, UK, using his methods described in "Modulation of the cold-activated channel TRPM8 by lysophospholipids and polyunsaturated fatty acids". Journal Neuroscience 27 (12): 3347-3355, 2007. Here, the cellular entry of the calcium-sensitive dye Fura-2 was used to study the effect of the test compounds on TRPM8 expressed in Chinese hamster ovary cells. Cells, grown in culture, were seeded at an approximate density of 30,000 cells/well overnight, and loaded for ~1 hr with 2 M Fura-2 (Molecular Probes, Leiden, The Netherlands), and then placed on glass coverslips. Test solutions were added with a micropipette positioned close to the cells. Emission intensity from cells was measured for 90 sec, at every 4 or 5 sec, using excitation wavelengths of 340 and 380 nm and an emission of 520 nm. Fluorescence emission intensity ratios at 340 nm/380 nm excitation (R, in individual cells) were recorded with a FlexStation and the ImageMaster suite of software (PTI, South Brunswick, NJ). Samples were tested in triplicate at each concentration and the averaged values analyzed by non-linear regression using an a sigmoidal function fit of the points to obtain an estimated EC50 (median effective concentration) (GraphPad Prism software, La Jolla, California).

Figure 5:
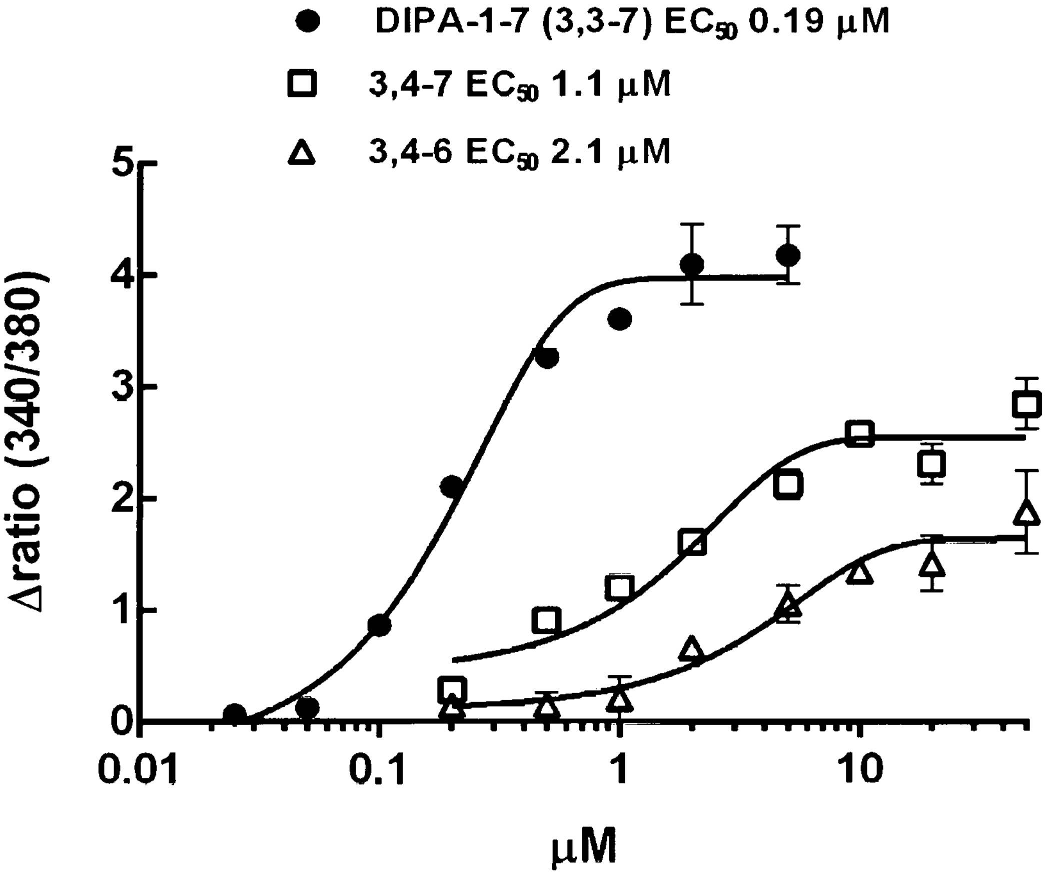
FIG. 5. is a graph of fluorescence response (Δ ratio 340/380) in TRPM8 transfected cells as a function of the logarithm of the concentration of the test compound, expressed in μM, for DIPA-1-7 (black circle), 3,4-7 (open squares), or 3,4-6 (open triangles). The assays were conducted by Andersson et al. of King's College, London, UK, using his methods described in "Modulation of the cold-activated channel TRPM8 by lysophospholipids and polyunsaturated fatty acids". Journal Neuroscience 27 (12): 3347-3355, 2007.

The potency of three analogs for activation of TRPM8 (cooling receptor) in transfected cells is shown in FIG. 5. The units (A ratio) on the ordinate measures entry of fluorescent calcium probes into transfected cells. The 3,3-7 (DIPA-1-7) is substantially more potent (~10× and ~5×) than 3,4-6 and 3,4-7. Note that 3,4-6 and 3,4-7 species do not reach the same degree maximal efficacy on activation of the receptor, even at supra-maximal concentrations.

FIG. 5. is a graph of fluorescence response (A ratio 340/380) in TRPM8 transfected cells as a function of the logarithm of the concentration of the test compound, expressed in μM, for DIPA-1-7 (black circle), 3,4-7 (open squares), or 3,4-6 (open triangles). The assays were conducted by Andersson et al. of King's College, London, UK, using his methods described in "Modulation of the cold-activated channel TRPM8 by lysophospholipids and polyunsaturated fatty acids". Journal Neuroscience 27 (12): 3347-3355, 2007.

From these results, it appears that the $EC_{50}$ values do not give information on the quality of the heat abstraction sensation, the duration of action, or the accessibility of the molecule to tissue targets. The identification of selective agents requires bioassays that more directly address these questions.

Study 5

Activity in Laboratory Rat: Perioral and Topical Delivery

Fur-coated and feathered animals—when wet and cold—shake, like a wet dog (see, e.g., Dickerson et al., 2012; Ortega-Jimenez et al., 2012; Wei, 1981). These shakes are rapid alternating contractions of the supination and pronation muscles about the spinal axis, and can be readily observed and counted. "Wet-dog shaking" has been studied in detail in animals and this behavior is interpreted to have survival value because shaking, by removing the water off the skin, reduces the need to expend evaporative energy to remove wetness. The triggering sensation for shaking is thus having water trapped in between hair follicles or feathers. Humans have little hair on skin and normally do not shake, but this wet shaking can be mimicked by some individuals who exit a cold swimming pool. The likely equivalent behaviour to shaking in humans is shivering, a condition caused by generalized sensations of coolness/cold and wetness.

Drug-induced shaking in animals has been reviewed (see, e.g., Wei, 1981). Under the right conditions, drug-induced shaking can be observed in the pentobarbital-anesthetized rat, enhanced by hypothermia and cold, and inhibited by elevating body temperature. Here, test compounds were evaluated for "wet-dog shaking" as a model of dynamic cooling. Using a standardized procedure, test compounds were compared in their ability to stimulate the shaking response by perioral administration and by topical delivery to the abdominal skin.

Perioral. Test compounds were dissolved in saline and administered by oral gavage to pentobarbital-anesthetized male albino rats at 20 mg/kg at a volume of 0.1 mL/100 g body weight [N=3 to 4 rats per compound]. Shaking was counted over a 40 min period and recorded at 10-min intervals.

Three of the four "di-isopropyl" compounds caused vigorous shaking. The "di-sec-butyl" compounds were relatively inactive, except 2-5 which elicited an average of 4 shakes in the 40 min observation period. By contrast, DIPA-1-5, DIPA-1-6, and DIPA-1-7 produced an average shaking frequency of 86, 56, and 36 shakes, respectively. The strong activity of DIPA-1-5 was unusual. Applied to the skin, DIPA-1-5 has a refreshing "dynamic cool", but the duration of action of about 30 min was significantly less than that for DIPA-1-6 and DIPA-1-7. The shorter duration of action of DIPA-1-5 limits its practical utility. It is possible that its smaller molecular size facilitates absorption and allows greater access to systemic receptors, and therefore more shaking. The relationship of the shake response to temperature sensation was further studied [in pentobarbital-anesthetized rats. After injection of the anesthetic, rectal temperature drops, and reaches approximately 35° C. in about 10 min. This hypothermia can be reversed by placing the animal on a heated surface and body temperature maintained at 38° C. DIPA-1-7 20 mg/kg perioral elicited 36±5 shakes (N=6) in the anesthetized rat, but in the heated animals, the shaking frequency was significantly reduced to 5±2 shakes (N=6) [P<0.001]. The reduction of shaking frequency by ⅔ under heat indicated that the shake response was linked to cold sensations and shivering.

Topical. Shaking is an excellent indicator of in vivo effect. Methods were developed to determine if shaking was seen after topical application of DIPA compounds. The abdominal skin of the pentobarbital-anesthetized rat was shaved and 20 μL of the pure DIPA was applied with a micropipette on a ~1 cm diameter circle of skin, enclosed with a ring of cream [Baby cream "Nevskaya kosmetika Detskyi" Nevskaya Kosmetika Inc., Saint-Petrsburg 192029], as shown in the FIG. 6. The number of shakes was counted for 1 hr after application.

Figure 6:
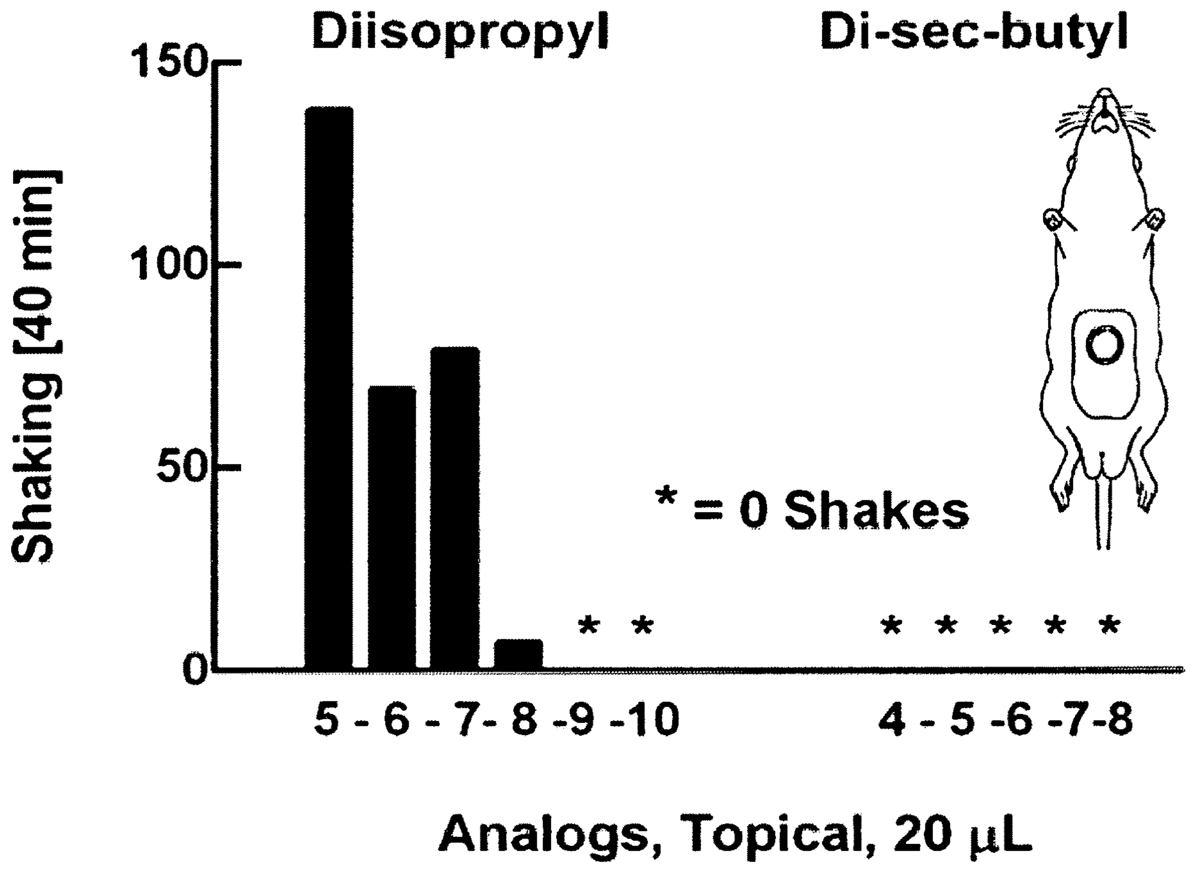
FIG. 6. shows the method for estimating the in vivo transdermal activity of the DIPA-embodiment compounds applied 20 μL with a micropipette to the center of a circle enclosed by cream on abdominal skin of an anesthetized rat. Shaking frequency was counted for 40 min after topical application. It can be seen that the embodiments DIPA-1-5, DIPA-1-6, and DIPA-1-7 evoke robust shaking, but this is not seen with other analogs.

FIG. 6 shows the method for measuring the transdermal activity of DIPA-compounds applied 20 μL with a micropipette to the center of a circle enclosed by cream on the abdominal skin of an anesthetized rat. Shaking frequency was counted for 1 hr after topical application. The data and results for topical for perioral responses are summarized in the Table 9. The data are further plotted graphically in FIG. 6, to show the lack of correlation of TRPM8 potency to in vivo bioactivity.

The data in Table 9 and FIG. 6 provide strong evidence for the novelty and exceptional properties for the compounds of this discovery. It is clear that these compounds penetrate biological membranes and rapidly evoke responses; events that are not seen with the comparative di-sec-butyl analogs. Furthermore, the bioactivity is not correlated to the potency measurement [$EC_{50}$] on the TRPM8 receptor. This is the first time that shaking responses of such magnitude have been shown after topical [dermal] application of a chemical.

TABLE 9

Shaking frequency after perioral [per 20 mg/kg body weight] or topical delivery of 20 μl test compounds [per animal] to the anesthetized rat.

| Code | Mol Wt | # Cs | Sensation | Perioral | Topical | xMenthol |
|---|---|---|---|---|---|---|
| DIPA-1-5 | 204 | 11 | dynamic cool | 86 ± 7 | 138 ± 15 | 0.7 |
| DIPA-1-6 | 218 | 12 | dynamic cool | 56 ± 5 | 69 ± 8 | 1.6 |
| DIPA-1-7 | 232 | 13 | dynamic cool | 36 ± 4 | 79 ± 8 | 5.4 |
| DIPA-1-8 | 246 | 14 | cool | 0 | 7 ± 2 | 5.4 |
| DIPA-1-9 | 260 | 15 | mild cool | 0 | 0 | 4.0 |
| 2-4 | 218 | 12 | cool | 0 | 0 | 0.3 |
| 2-5 | 232 | 13 | cool | 4 ± 1 | 0 | 2.2 |
| 2-6 | 246 | 14 | cool | 0 | 0 | 4.7 |
| 2-7 | 260 | 15 | cool | 0 | 0 | 3.4 |
| 2-8 | 274 | 16 | cool | 0 | 0 | 2.9 |

Surprisingly, vigorous shaking was evoked with inventive embodiments DIPA-1-5, DIPA-1-6, and DIPA-1-7. Only a weak response was seen with DIPA-1-8, and the comparative di-sec-butyl analogs, 2-5, 2-6, and 2-7, were inactive. The shaking induced by DIPA-1-7 was dose-dependent. Topical application of 5 μl, 10 μl, 20 μl, or 50 μl of DIPA-1-7 elicited an average of 25±3, 53±6, 79±8 and 118±12 shakes, respectively, in 1 hr. Shaking was seen if DIPA-1-7 was diluted 50-50 with either water or saline (at the 10 μl dose), but it was completely inhibited if 50% (R)-1,2-propanediol was added to the DIPA-1-7 (at the 10 μl dose) as a diluent. This surprising result shows that DIPA-1-7 penetrates the skin in aqueous solution and is retarded by an alcoholic solvent. This facile permeability of DIPA-1-7 is reminiscent of menthol, and suggests DIPA-1-7 is easily delivered into the dermis by topical application. Furthermore, DIPA-1-7 may be used to penetrate thick keratotic skin lesions, for example in psoriasis or in contact dermatitis of the hands, to alleviate itch and pain. The adjustment of DIPA-1-7 concentrations in polyhydric solvent such as 1,2-propanediol can be used to control the degree of absorption of DIPA-1-7, an art well-known to formulation experts.

The surprising potency of DIPA-1-5 and DIPA-1-6 was unexpected. These molecules work for a shorter time on skin cooling than DIPA1-7. These smaller molecules may penetrate faster through the skin barrier and go into the systemic circulation. However, the value of this fast action is uncertain. In most contemplated topical applications of this discovery, the preference is for the drug action to remain localized and not systemic. When the relative activities of the analogs for producing shaking are compared to the $EC_{50}$ for TRPM8 activation, it can be seen that the two variables are not correlated. The limitations of the TRPM8 $EC_{50}$ for predicting bioactivity were discussed earlier.

The results here provide the strongest objective laboratory evidence that the DIPA compounds of Formula 1 selectively produce vigorous “dynamic cool”. The total number of carbons, or the number of carbons in the largest alkyl group, did not correlate to the magnitude of bioactivity. The key factor to penetration was to avoid masking the phosphine oxide group.

Study 6

Water Solubility and Penetration to Target The receptor targets on the nerve endings are embedded in the epithelial cell layers. The epidermis is only ~1 mm thick, but the stratum corneum, with its layers of dead cells and denatured proteins, impedes access of the agonist molecule to the nerve endings. The heel of the feet has the thickest barrier, 86 cell layers, followed by the palm of the hand, then the back of the hand. If you put an ice cube on the heel, you feel a bit of cold: but you will jump when you put it on the sole of the feet which has fewer layers. Unless the skin of these surface are structurally damaged, e.g. by inflammation, applying a cooling agent will not work, because the molecules do not access the nerve endings. For other surfaces, the genital skin (glans of the penis and vulva) and the eyelids are the thinnest, with 4 to 8 cell layers. The extremities, arms and legs, and the trunk (torso) have thicker surfaces. The scalp is intermediate. The face varies: the cheek is relatively insensitive, but areas around cheekbone and nasolabial folds are thin and sensitive. These differences are important for drug action. For itching of the flexures of the limbs, e.g. elbow and knees, you need good drug penetration. For the eyelids and genital skin, you must choose your molecule carefully to get the desired effects with gentle cooling and avoid too much stimulation.

By contrast to the compounds tested by ’496, applicant’s preferred embodiments of DIPA-1-7, DIPA-1-8, and DIPA-1-9, wherein two of the alkyl groups (e.g. $R_2$ and $R_3$) are both isopropyl, have high water solubility and skin penetration. Increasing water solubility to increase bioactivity is counterintuitive in standard drug design. Normally, formulation experts try to break down the stratum corneum with enhancers and chemists try to increase lipid solubility of the molecule (e.g. M. Prausnitz et al. Skin barrier and transdermal drug delivery. Chpt. 124, Medical Therapy, 2012). Nevertheless, the strategy used here was met with clinical success.

For the equivalent number of total carbons and hence equal molecular weights, applicant find that DIPA are at least 2 to 3× more water soluble than DAPA. In the DIPA series the polar phosphine oxide is not masked by the extra branched chain carbons. The DIPA are more hydrophilic than DAPA. Studies of skin permeation in vitro on hairless mouse skin confirmed the unusual penetrating power of the DIPA structure. In in vivo laboratory animals the pharmacological differences of the DIPA from DAPA congeners were strikingly different. Both DIPA and DAPA were active by intravenous injection, but only DIPA was active by topical or oral routes of administration, indicating penetration across the dermal and gastrointestinal membranes of DIPA, but not DAPA structures.

Figure 7:
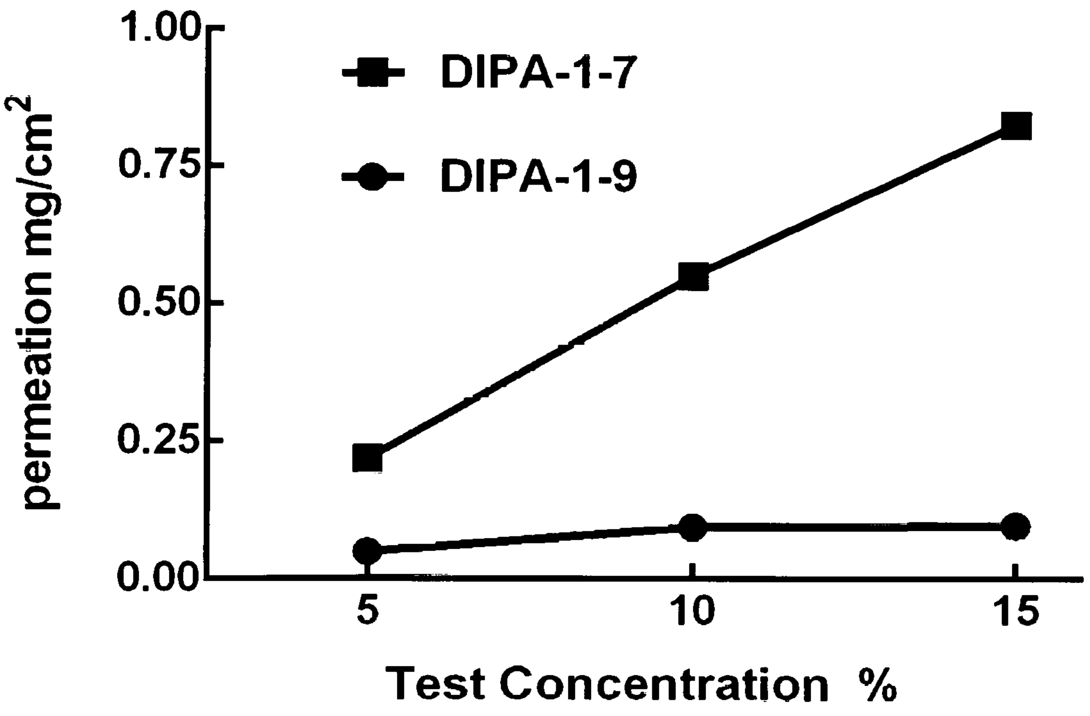
FIG. 7. shows the flux of DIPA-1-7 and DIPA-1-9 through excised hairless mouse skin in vitro. Test chemicals dissolved in a gel were placed in an incubator for 8 hr and the permeated amount of the chemical measured by a high pressure liquid chromatograph equipped with a refractive detector. These tests were conducted by Prof Choi of Chosun University, Korea. The flux of 1-7 was ~5× greater than 1-9. Standard enhancers with polyhydric alcohols, such as a propylene glycol-oleyl alcohol mixture (50:50) or Lauroglycol 90, designed to increase permeation added to the 1-7 gel decreased the rate of permeation by ~50%, indicating the importance of water solubility for permeation.

To further study the skin permeation of DIPA compounds, tests were conducted on the flux of DIPA-1-7 and DIPA-1-9 through excised hairless mouse skin in vitro (FIG. 7). Standard enhancers with polyhydric alcohols, such as a propylene glycol-oleyl alcohol mixture (50:50) or Lauroglycol 90, designed to increase permeation added to the 1-7 gel decreased the rate of permeation by ~50%, indicating the importance of water solubility for permeation. In studies on the abdominal skin of anesthetized rat, it was found that a 50:50 propylene glycol-DIPA-1-7 mixture was inactive when tested on the skin of animals, with shaking as an endpoint, whereas the pure DIPA-1-7 was very active. Thus, normal solvents or enhancers of dermatological molecules impede rather than facilitate passage of the DIPA through skin barriers.

FIG. 7. shows the flux of DIPA-1-7 and DIPA-1-9 through excised hairless mouse skin in vitro. Test chemicals dissolved in a gel were placed in an incubator for 8 hr and the permeated amount of the chemical measured by a high pressure liquid chromatograph equipped with a refractive detector. These tests were conducted by Prof Choi of Chosun University, Korea. The flux of 1-7 was ~5× greater than 1-9. Standard enhancers with polyhydric alcohols, such as a propylene glycol-oleyl alcohol mixture (50:50) or Lauroglycol 90, designed to increase permeation added to the 1-7 gel decreased the rate of permeation by ~50%, indicating the importance of water solubility for permeation.

The mobility of the DIPA molecules in an aqueous environment through a skin barrier is unusual and surprising. Apparently, if the polar “head” is masked by one or more carbon (e.g. methyl) groups, water solubility and permeability decrease. Alternatively, the symmetrical (achiral) arms (the isopropyl groups) may enable an efficient swimming of the DIPA through the pores of the stratum corneum and into the extracellular fluid, until the TRPM8 receptors in the stratum basale are reached. The DIPA configuration may be viewed as a “sperm” like head (the oxygen cloud about the phosphorus atom) that permits a polar interaction with water. The “swimming” motion may be impaired if the branched arms are asymmetrical (chiral).

Study 7

Effects on Topical Sites on the Cranium. DIPA-1-7, the most potent compound for dynamic cooling, was tested at topical sites on the cranium. A 20 mg/mL solution was applied, using a cotton wipe, onto the skin above the buccal cheek, the parotid-masseteric cheek, temple, and the skin above the periauricular region, and the posterior mandible using the appropriate craniometric points (pterion, coronion, condylion, and gonion, respectively) as landmarks. At these sites, other than the buccal cheek, little cooling was observed. Mild cooling was observed on the buccal cheek for approximately 30 minutes, but this effect may have been due to the spread of the solution onto the receptive field of the infraorbital nerve. It should be noted, however, the sensory effects of topical application of DIPA-1-7 may be influenced by inflammatory lesions that can alter permeability, for example, seborrheic dermatitis or psoriasis. In these conditions DIPA-1-7 is highly effective for itch.

The head is known to be a site where cooling helps relieve heat discomfort. In a study described in Nakamura et al. [2012], eleven male subjects were exposed to mild heat. Subjects, clothed in only short pants, entered a climatic chamber maintained at 32.5±0.5° C. with a relative humidity of 50%. About 1.5 hours after entry into the chamber, a local cooling protocol was initiated with water-perfused stimulators placed on the head, chest, abdomen, or thigh. Cooling of the face and thigh was felt by the subjects to be more effective than cooling of the chest and abdomen in reducing the heat discomfort.

In a study described by Essick et al. [Site-dependent and subject-related variations in perioral thermal sensitivity. Somatosensory & motor research 21, 159-75, 2004] the thresholds for detection of cooling and cold pain on various sites of the face, ventral forearm, and scalp was determined for 34 young adults. The most sensitive sites were on the vermilion which could detect a temperature change of about 0.5° C., followed by areas around the mouth (upper and lower hairy lip, mouth corner) and lateral chin. The mid-cheek and periauricular skin were less sensitive (able to detect a temperature change of about 2° C.), and the forearm and scalp were least sensitive (able to detect a temperature change of about 3° C.). The sensitivities of the orbital, zygomatic and forehead skin were not tested.

Case Studies

Case studies are described below which demonstrate the use of DIPA in dermatological disorders; (a) contact dermatitis, and atopic dermatitis: to counteract skin itch and pain in subject experiencing these dermatological symptoms (b) dry skin of the elderly: to break the "itch-scratch" cycle (c) urticaria: to reduce symptoms (d) to reduce the symptoms of cholestatic itch in a patient with liver disease, (e) scalp itch f) cholestatic itch, g) ocular itch: to attenuate the discomfort of eyelid inflammation and (h) lichen sclerosus: to treat the discomfort of genital inflammation. Comparison was also made among the DIPA analogs for efficacy. For several of these conditions, including urticaria and cholestatic itch, the surprise was the DIPA compounds were effective even when the keratinized skin is "intact", i.e. the stratum corneum is normal, and one would not expect a topical medication to penetrate and to be active.

In these studies, subjects were given DIPA-1-7, 1.5% wt./vol commercial gel (Intrinsic B, Dong Wha Pharmaceuticals, Seoul, Korea) or in individual dosages units containing 1.5 to 1.75 mL of DIPA-1-7 stored in 2.0 mL microcentrifuge tubes (Nova Biostorage Plus, Canonsburg, PA 15317) and cotton gauze (0.4 g, rectangular, 50 mm×60 mml; from CS-being, Daisan Cotton, Japan). For the wipes, the DIPA-1-7 was provided as a solution in distilled water, at a DIPA-1-7 concentration of 5 mg/mL to 20 mg/mL. The subjects were given instructions on how to place wet the gauze and how to wipe over the skin. Approximately 0.15 mL to 0.35 mL per unit wipe was delivered by these methods of application. Subjects were instructed to rinse with water if any surface becomes irritable; however, irritation and discomfort were not seen with DIPA-1-7, DIPA-1-8, or DIPA-1-9 at the test concentrations.

Case Study 1

Contact dermatitis. Two scientists working in the laboratory had allergic dermatitis of the hand in response to detergents and soaps. The hands were inflamed and extremely itchy. Applications of DIPA-1-7, 20 mg/mL, with a cotton-tipped applicator or gauze immediately stopped the itch and this effect lasted for at least 2 hours, and the suppression could be renewed by repeated application. One scientist, a world-renowned dermatologist with many publications on itch, noted that the DIPA-1-7 produced an "icy-cool" feeling on the inflamed skin and he had never encountered such a compound that was so effective in stopping itch so quickly.

A pharmacologist liked to work in the garden, but the thorns from bougainvillea stems and rose bushes, and the hair from azalea leaves, irritated his skin and caused intense itch. He noted that the sensory discomfort on the skin could be instantly stopped by DIPA-1-6 or DIPA-1-7, applied either as a 20 mg/mL aqueous solution, or as a cream (mixed with Eucerin Moisturizing Cream). These effects could also be obtained with DIPA-1-8. He also noted that the irritation and itch caused by insect bites could be immediately stopped by these agents.

Case Study 2

Atopic dermatitis. An 8-year old boy had atopic dermatitis since childhood and exhibited the standard scars on the flexures of his elbow and knees. He had been treated with topical steroids, but the skin had become thin and easily broken. He objected to topical ointments because of the excessive "greasy" feel and stickiness, and because he felt they were not effective in stopping the itch. He also used moisturizers. The itch interfered with his sleep, especially during periods when his allergic rhinitis flared up. His parents were concerned with the scratching at night, poor scholastic performance, and lack of concentration. The subject was given 8×8 cm wipes saturated with 2 mL of DIPA-1-7 at 10 mg/mL in water, and given instructions to use the wipes after washing, to wipe over skin sites that itched in the evening, as he prepared for sleep. The wipes were immediately effective in reducing itch and scratching and facilitated sleep. Over a 2-week period of use, the skin lesions became less red, formed scabs, and progressed to heal. It was clear that the itch-scratch cycle had been attenuated. The boy became more cheerful and he paid more attention to his schoolwork. His parents were extremely pleased.

Case Study 3

Pruritus and Xerosis of the Elderly an eighty-six year old retired widower decided to move from California to a hotel suite in Hong Kong for permanent residence. He had been an avid and skilled golfer for many years and had actinic keratosis and a dry skin. Over time, his skin became itchy, especially on the forearms and back torso. Scratching with a wooden stick on his back at first helped, but the skin became damaged, infected, and inflamed. He applied Eucerin's "Atopic Control" which helped relieve the dryness, but found it to be expensive, heavy and "greasy", although it definitely provided some protection and relief. The itching and inflamed skin became unbearable during the hot summer months in Hong Kong, when the air conditioning was on full blast, and during the dryness of the fall season. His dermatologist prescribed a potent topical steroid, but his skin became fragile, infected, and ulcerated in some areas. His life was miserable because of the skin discomfort. He agreed to try a DIPA-1-8 solution, 10 mg/mL in isotonic saline. He applied about 20 drops of the DIPA-1-8 onto an 8×8 cm wipe made of 100% viscose 50 grams per square meter. After wiping, the volume off-loaded onto his skin was about 0.2 to 0.25 mL, so the total dose per wiping was 2 to 2.5 mg. The topical application of the DIPA-1-8 relieved his itch within 3 to 5 min after wiping, and he stopped complaining of skin discomfort. His live-in nurses remarked that he no longer scratched as much. He said the wipes when applied to the face, also gave the sensation of wetness, and thus may be useful for cosmetic applications. He continued the use of the wipes on an as need basis and his skin, formed scabs, healed, and resumed a normal appearance. His only negative comment was that the solution made him feel too cool when the air conditioning was on a high setting. He continued using the wipes until death from a bulbar stroke three years later.

Case Study 4

Urticaria. Urticaria (hives) is an allergic condition in humans manifested by skin rashes (wheals). The symptoms of redness, swelling, and itch on the skin are caused primarily by release of histamine from mast cells into the dermal layers. A frequent trigger for hives is the ingestion of seafood. Here is a description of a case of urticaria treated with DIPA-1-7, formulated 1.5% wt./vol in a gel made by Dong Wha Pharmaceuticals (Seoul, Korea). A female subject with a history of hives went to a seaside resort in the South of France and consumed over two days seafood pasta, minced crab, and mixed seafood soups. She developed extensive welts on her buttocks with the classic signs of inflammation, namely, "calor" (heat on touch of the inflamed tissues), "rubor" (redness caused by vasodilatation), "tumor" (swelling) and "dolor" (pain and itch). Wheals also appeared on the skin above the clavicle and on her neck. It was distressing. Application of the gel on the skin diminished all four signs of inflammation beginning about 5 to 10 min after application. The subject described the effect as "burning cold" and then robust cool, but excellent for decreasing the sense of itch and "heat" from the red welts. Swelling, redness, and "flare" were visibly diminished 30 min after application. The gel was applied again 3.5 hr later, and then the subject given three tablets of fexofenadine (120 mg) and a tablet of chlorphenhydramine (4 mg). All the signs and symptoms of the hives were viewed as being diminished by at least 50% and "under the control" by the subject in 12 hr, and the skin rashes disappeared after three days and did not recur.

This is the first report in which the skin dysesthesia (itch and a sense of heat) and other signs of inflammation caused by urticaria are reduced rapidly after topical medication (1.5% DIPA-1-7 in a gel). The rapid effectiveness of DIPA-1-7 applied to the relatively thick skin of the buttocks (15 to 18 cell layers of stratum corneum) indicated permeation to the nerve endings that allowed the symptoms and signs of inflammation to be alleviated. The therapeutic effect and rapid onset is of sufficient intensity to benefit the patient. Additional case studies with DIPA-1-7 gel in 8 cases of urticarial dermatoses were obtained by an established dermatologist in a leading hospital in Seoul, Korea. The satisfactory suppression of itch was obtained in 75% of patients. In this study, there were also 5 cases of atopic dermatitis, 6 cases of seborrheic dermatitis, 3 cases of prurigo nodularis, and 3 cases of herpes zoster. In the cases tested, the skin dysesthesia intensity was assessed on a visual analog scale after use of DIPA-1-7 for one week. It was clear that the DIPA-1-7 gel had benefits in a variety of dermatological disorders. These results have now been published in Jung M J, Kim J C, Wei E T, Selescu T, Chung B Y, Park C W, et al. A randomized, vehicle-controlled clinical trial of a synthetic TRPM8 agonist (Cryosim-1) gel for itch. J Am Acad Dermatol 84(3):869-71.

Case Study 5

Scalp Itch. The scalp is a frequent site of itch. Topical treatment is practical, but the target and pathological lesion are frequently difficult to visualize. Factors such as hair, sebum, and the thickness of the scalp also affect drug penetration to target. Hence, effective treatment of scalp itch is an unmet medical need. A frequent trigger for scalp itch is the use of hair dyes. Scratching of the scalp can also increase under psychogenic stress, but scratching is considered unsanitary and met with social prejudice. We have conducted a study on human subjects with scalp itch and published the results [Kang S Y, Choi M G, Wei E T, Selescu T, Lee S Y, Kim J C, et al. TRPM8 agonist (cryosim-1) gel for scalp itch: A randomized, vehicle-controlled clinical trial. J Eur Acad Dermatology Venereol. 2022; 1-2]. Subjects with scalp itch were treated with DIPA-1-7, formulated 1.5% wt./vol in a gel made by Dong Wha Pharmaceuticals (Seoul, Korea). A total of 25 to 31 subjects with scalp itch participated. There was clear-cut and significant relief of scalp itch in the subjects tested. This is the first double-blind report in which a topical cooling agent was used to treat scalp itch. The therapeutic effect and rapid onset is of sufficient intensity to benefit the patient. In these patients there was intense itching, but no visible lesions on the scalp.

Case Study 6

Cholestatic Itch an 80-year renowned Professor of History was diagnosed with terminal liver cirrhosis and developed a severe disseminated itch. His children learned of the DIPA anti-itch medication and requested samples because the subject was constantly itching and scratching. The subject's skin was intact and there were no rashes. The condition was diagnosed as cholestatic itch. The subject was given cotton gauze squares and 30 mL plastic dropper bottles containing 2% DIPA-1-7 in water. He was instructed to wet the squares and wipe the solution on the site of itch on an as needed basis. The subject declared after his first trial that this was the best medication he had ever tried for the itch and that it worked. He used about one 30 mL bottle every three days and demanded more. This regimen continued until the subject expired three months later.

Case Study 7

Ocular Itch of Various Etiologies. A 28-year old female subject visited her optometrist with complaints of dry eye disease disorder, namely, a sense of discomfort from the eye surface, blurring of vision, burning sensations, sensitivity to light, and problems with reading, driving, and using the smartphone screen. Upon examination, she was found to have hyperaemia of the eyelid margins, blockage of the Meibomian gland ducts, some thickening of the eyelid margins indicating epithelial hyperkeratinisation, and makeup debris in the eyes. Further questioning revealed that she was using a bimatoprost solution to induce hypertrichosis, but was applying the solution two or three times of a day (instead of the suggested single application per day) because she was dissatisfied with the slow rate of eyelash growth.

She was diagnosed with blepharitis and conjunctivitis and instructed not to use eye makeup and given Blephaclean™ eye wipes, which are single unit wipes with a cleansing solution, to clear the Meibomian gland ducts and to maintain eye hygiene. The subject, however, objected vehemently to the irritation caused by the cleansing wipes and her inability to continue use of the bimatoprost solution, which was quite expensive. The subject was recruited into a clinical trial of a DIPA-1-9 wipe, 2 mg/mL in water, and instructed to use the wipe once in the morning, once in the evening, and two more wipes on an as needed basis during the day. She felt immediately better upon using the DIPA-1-9 wipes and commented on the cooling and refreshing sensations that were now present on her ocular surface and margins. She said her bimatoprost solution now no longer irritated and her eyelashes were now thick and luxurious. The blepharitis and conjunctivitis was gone. She recommended that the DIPA-1-9 be added to the bimatoprost solution as an adjunct. She offered to pay for a continued supply of the DIPA-1-9 wipes.

More recent studies on treatment of ocular disorders in human subjects have been published (Yoon H J, Kim J, Yang J M, Wei E T, Kim S J, Yoon K C. Topical TRPMB Agonist for Relieving Neuropathic Ocular Pain in Patients with Dry Eye: A Pilot Study. J Clin Med. 2021; 10(2):250).

Case Study 8

Lichen sclerosus. A 40-year old suffered from penile lichen sclerosus. This is an inflammatory dermatosis of the glans penis and foreskin and, in this particular case, was associated with intense pruritus and dysesthesia (burning sensations). The patient, under the supervision and care of his dermatologist, volunteered to try DIPA-1-8 on his lesion and he was supplied with various concentrations of DIPA-1-8 dissolved in distilled water. After self-experiment, he concluded that concentrations of 1 to 1.5 mg/mL of DIPA-1-8 produced significant relief, but a concentration of 2 mg/mL of DIPA-1-8 was too cold and uncomfortable. The solutions were applied with cotton-tipped applicators or gauze wipes. The advantage of using DIPA formulations for genital skin is water solubility. This minimizes the need for excipients and the likelihood of further irritation. The subject suggested that an aerosolized spray may also be a convenient method of drug delivery.

The availability of a commercial sample of 1.5% DIPA-1-7 gel called Intrinsic B in Korea has permitted further assessment in several female patients with lichen sclerosus. These patients noted the gel produced strong tingling at first when applied to crusted wounds caused by scratching, but they said the gel helps to suppress the scratching behavior caused by paroxysmal itch in social situations. Another population benefiting from a DIPA wipe is post-menopausal women with a history of breast cancer. Hormonal replacement therapy (HRT) cannot be used for this group and with age the vulvar epithelium atrophies together with a reduction of vaginal secretions. These conditions lead to pruritus which is alleviated by the use of a 1% DIPA-1-8 wipe.

These studies illustrate the anti-nociceptive properties of DIPA-1-7 and DIPA-1-8, especially on genital itching. DIPA-1-8 had a longer duration of action than DIPA-1-7, and may be the preferred agent for dermatological applications. Further studies showed that DIPA-1-9 at 2 mg/mL applied with a wipe on the glans or on the vulva produced that a gentle cooling and refreshing sensation that counteracted any inflammatory discomfort.

Case Study 9

Three subjects decided to systemically compare DIPA-1-6, DIPA-1-7, DIPA-1-8, and DIPA-1-9 for their sensory effects on the ocular surface. Each compound was prepared at 1 mg/mL in distilled water. A cotton tipped applicator of a specific size (Puritan 803-PCL) consisting of a 55 to 75 mg ball of cotton wound around the tip of a three inch polystyrene rod was dipped into the solution. The tip was then applied, with the eyelids closed, to the lower aspect of the upper eyelid, onto the eyelashes, with two lateral to medial wiping motions. The subjects were then instructed to blink. By blinking, the solution is then evenly distributed over the pre-corneal film. This "swab" delivery method off-loaded a total of ~35 μL of liquid onto the surface of both eyes. DIPA-1-6 caused significant stinging and discomfort and was therefore not further studied. DIPA-1-7 and DIPA-1-8 produced strong and refreshing cooling, which counteracted eye irritation, and increased cognitive functions. For example, subjects felt they could focus on distant objects and enjoy the view. They felt mentally alert and refreshed. But, with both DIPA-1-7 and DIPA-1-8, there was a small residue left on the eyelid; subsequently using a towel to wash the face can cause eye irritation. Surprisingly, DIPA-1-9 did not produce any eye irritation when wiped over the eyelid, nor did it leave a residue. It also produced refreshing cooling, but not with the same intensity as DIPA-1-7 or DIPA-1-8. On the other hand, DIPA-1-9 has ideal properties for the treatment of ocular discomfort, e.g., discomfort caused by eye strain; eye fatigue; eye surgery; an airborne irritant or pollutant that interacts with the eye surface; extended wear of contact lenses; excessive exposure to the sun; conjunctivitis; conjunctivitis in atopic dermatitis patients treated with dupilumab; or the dry eyes syndrome. Some of these results have been published in Yang J M, Li F, Liu Q, Rüedi M, Wei E T, Lentsman M, et al. A novel TRPM8 agonist relieves dry eye discomfort. BMC Ophthalmol. 2017; 17(1). These towelettes for the treatment of ocular discomfort and asthenopia are available as a product called OcuCool in the Republic of Korea. Of special interest is the good efficacy of OcuCool in treating the itch of conjunctivitis in atopic dermatitis patients receiving dupilumab.

Summary of Observations

The structures of Rowsell and Spring '496 were described 40+ years ago, but were not developed for use. The applicant found that diisopropyl analogs were not described in '496. He then synthesized and tested these analogs. The "head" of the prototypical DIPA molecule is polar (hydrophilic) and soluble in the polar environment of water. This increased water-solublility of the analogs paradoxically facilitates permeation past dead cell layers of the stratum corneum to access receptors in skin nerve endings. The preferred embodiments, 1-7 and 1-8 exert a robust cold sensation that can modulate skin dysesthesia caused, for example, by various dermatitis (e.g. atopic or urticaria) and by dryness (xerosis). This occurs in dermatological disorders wherein the skin is intact, e.g., urticaria, cholestatic itch. On marginal transitional epithelium of the eyelids and anogenitalia DIPA-1-9 is surprsingly active, but without the "icy cold" effects of DIPA-1-7.

For the equivalent number of total carbons and hence equal molecular weights, applicant find that DIPA are about 10× more water soluble. Studies of skin permeation in vitro on hairless mouse skin confirmed the penetrating power of the DIPA. In in vivo laboratory animals the pharmacological differences of the DIPA from the mixed isopropyl/sec-butyl and di-sec-butyl congeners were strikingly different. Both DIPA and di-sec-butyl were active by intravenous injection, but only DIPA was active by or topical or oral routes of administration, indicating better penetration across the dermal and gastrointestinal membranes of the DIPA, but not di-sec-butyl structures. The ability of the DIPA structures to relieve skin discomfort in patients with an intact stratum corneum and a dermatological disorder was rapid, dramatic, and unexpected.

The '496 structures have their "head" covered by more lipophilic groups and are chiral, and are less able to permeate to target receptors in the basal layers of the skin to achieve the same therapeutic endpoints as the preferred embodiments. Increasing water solubility is counterintuitive in standard drug design for enhancement of transdermal drug permeation. Normally, formulation experts try to break down the stratum corneum with enhancers and chemists try to increase lipid solubility of the molecule (e.g. M. Prausnitz et al. Skin barrier and transdermal drug delivery. Chpt. 124, Medical Therapy, 2012). Nevertheless, the strategy used here was met with clinical success. These observations are now buttressed by publications of well-designed trials in reputable journals. Thus, the applicant opines that the discovery of the DIPA embodiments for dermatological disorders is a quantum jump of improvement in the discovery process.

References. A number of publications are cited herein in order to more fully describe and disclose the discovery and the state of the art to which the discovery pertains. Each of these publications is incorporated herein by reference in its entirety into the present disclosure.

The invention claimed is:

1. A method for the treatment of blepharitis or conjunctivitis in a subject in need thereof, comprising:

topically applying a liquid or semi-liquid composition to an ocular surface or an area of periorbital facial skin of the subject, the composition comprising a therapeutically effective amount of one or more compounds having Formula 1 dissolved therein Formula 1

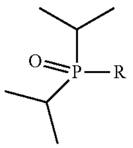

wherein R is n-heptyl, n-octyl or n-nonyl; and wherein the conjunctivitis is caused by administration of dupilumab to a subject with eczema.

2. The method of claim 1, wherein the composition is topically applied to the subject's ocular surface.

3. The method of claim 1, wherein the composition is topically applied to an area of periorbital facial skin of the subject, wherein the area of periorbital facial skin comprises an eyelid.

4. The method of claim 1, wherein the liquid or semi-liquid composition comprises from about 0.05 to 2% by weight of the one or more compounds of Formula 1.

5. The method of claim 1, wherein the composition comprises the one or more compounds of Formula 1 at a concentration of 1-20 mg/ml.

6. The method of claim 1, wherein the composition is a liquid composition comprising the one or more compounds of Formula 1 at a concentration of 1-5 mg/mL.

7. The method of claim 1, wherein the subject is in need of treatment for blepharitis.

8. The method of claim 1, wherein the subject has eczema and is in need of treatment for conjunctivitis caused by administration of dupilumab.

* * * * *